(12) United States Patent
Stender et al.

(10) Patent No.: US 11,065,372 B2
(45) Date of Patent: Jul. 20, 2021

(54) NEEDLE SYSTEM RESTRICTOR

(71) Applicant: Gyrus ACMI, Inc., Southborough, MA (US)

(72) Inventors: Eric Stender, Champlin, MN (US); Kester J. Batchelor, Mound, MN (US); Huisun Wang, Maple Grove, MN (US)

(73) Assignee: Gyrus Acmi, Inc., Westborough, MA (US)

( * ) Notice: Subject to any disclaimer, the term of this patent is extended or adjusted under 35 U.S.C. 154(b) by 508 days.

(21) Appl. No.: 15/937,451

(22) Filed: Mar. 27, 2018

(65) Prior Publication Data
US 2019/0298898 A1    Oct. 3, 2019

(51) Int. Cl.
| *A61M 1/00* | (2006.01) |
| *A61B 8/12* | (2006.01) |
| *A61B 10/02* | (2006.01) |
| *A61B 10/04* | (2006.01) |

(52) U.S. Cl.
CPC ........... *A61M 1/0049* (2013.01); *A61B 8/12* (2013.01); *A61B 10/0283* (2013.01); *A61B 2010/045* (2013.01); *A61M 2210/1035* (2013.01)

(58) Field of Classification Search
CPC ........ A61M 1/0049; A61M 2210/1035; A61B 8/12; A61B 10/0283; A61B 2010/045; A61B 1/00087; A61B 1/00131; A61B 1/005; A61B 1/267; A61B 1/2676; A61B 2017/00349; A61B 2217/005; A61B 10/02; A61B 10/0208; A61B 10/0233
USPC ........................................................ 600/566
See application file for complete search history.

(56) References Cited

U.S. PATENT DOCUMENTS

| 5,060,658 | A  | * | 10/1991 | Dejter, Jr. | A61B 10/0283 |
| | | | | | 600/566 |
| 7,179,232 | B2 | * | 2/2007 | Sutton | A61B 10/025 |
| | | | | | 600/562 |
| 8,701,658 | B2 | | 4/2014 | Mazela et al. | |
| 9,909,103 | B2 | * | 3/2018 | Howard | C12N 5/0653 |
| 2006/0009712 | A1 | * | 1/2006 | Van Bladel | A61B 18/02 |
| | | | | | 600/566 |
| 2007/0106176 | A1 | * | 5/2007 | Mark | A61B 10/0266 |
| | | | | | 600/566 |
| 2008/0221580 | A1 | * | 9/2008 | Miller | B23B 45/00 |
| | | | | | 606/80 |

(Continued)

FOREIGN PATENT DOCUMENTS

| EP | 2546523 A2 | 1/2013 | |
| WO | WO-2016153770 A1 | * 9/2016 | .......... A61B 10/0266 |

OTHER PUBLICATIONS

FruitFlyFunnel, 2016, Accessed Mar. 27, 2018, http://fruitflyfunnel.com/4-simple-steps/, 3 pages.

(Continued)

*Primary Examiner* — David J. McCrosky
*Assistant Examiner* — Chanel J Jhin
(74) *Attorney, Agent, or Firm* — Schwegman Lundberg & Woessner, P.A.

(57) ABSTRACT

A needle system a handle and a needle slider partially positioned in the handle. The needle slider has an aspiration port at a proximal end of the needle slider. A needle connected to and extending away from the needle slider. A restrictor is disposed in the aspiration port of the needle slider. The restrictor is configured to inhibit passage of a sample through the aspiration port.

15 Claims, 19 Drawing Sheets

(56) References Cited

U.S. PATENT DOCUMENTS

2012/0089236 A1    4/2012  Errico et al.
2016/0367231 A1   12/2016  Uemichi et al.

OTHER PUBLICATIONS

Bukyung, Eel Trap, 2018, Accessed Mar. 27, 2018, https://bukyung.en.ec21.com/Eel_Trap—1508906_2826244.html, 3 pages.

* cited by examiner

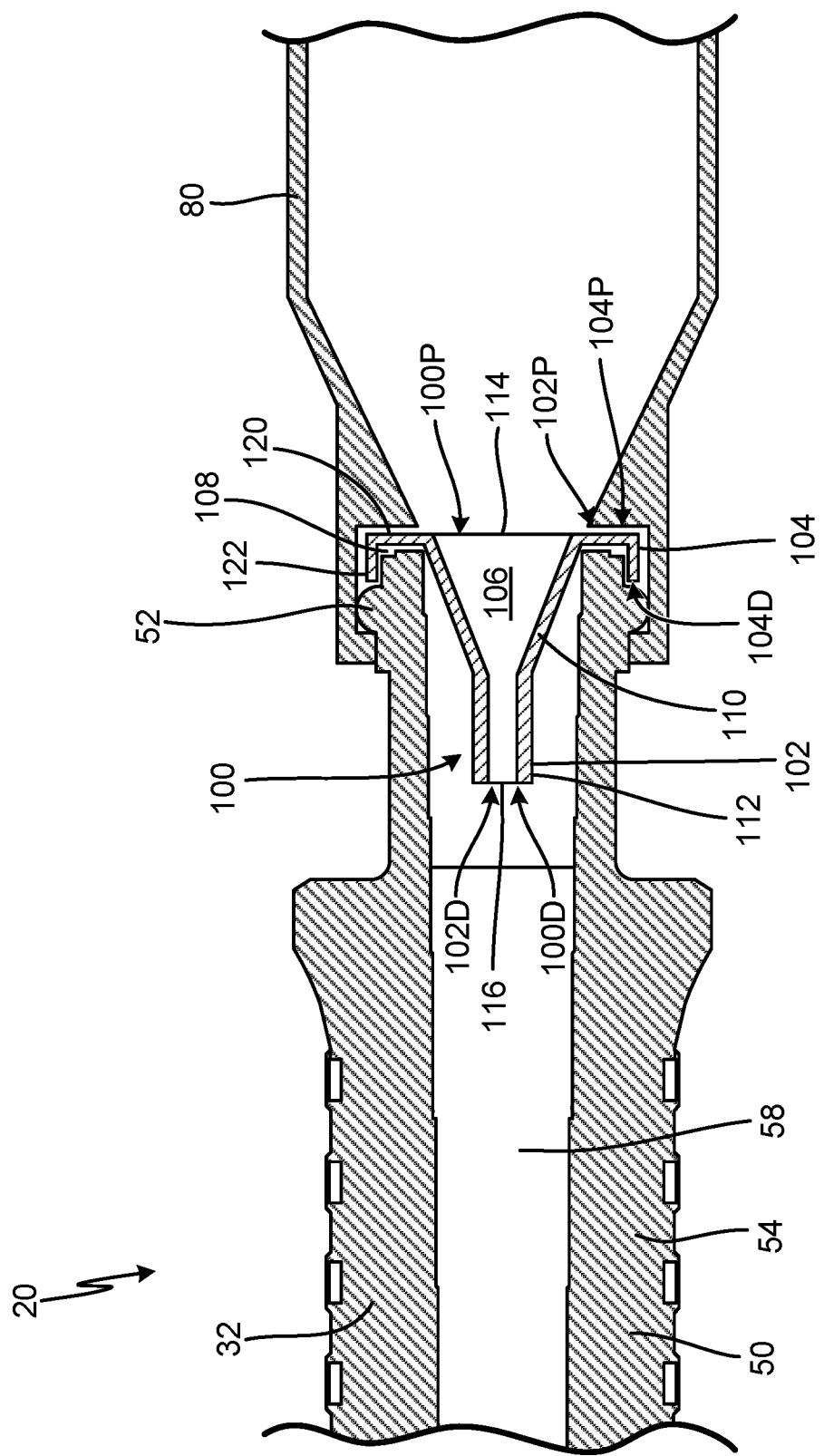

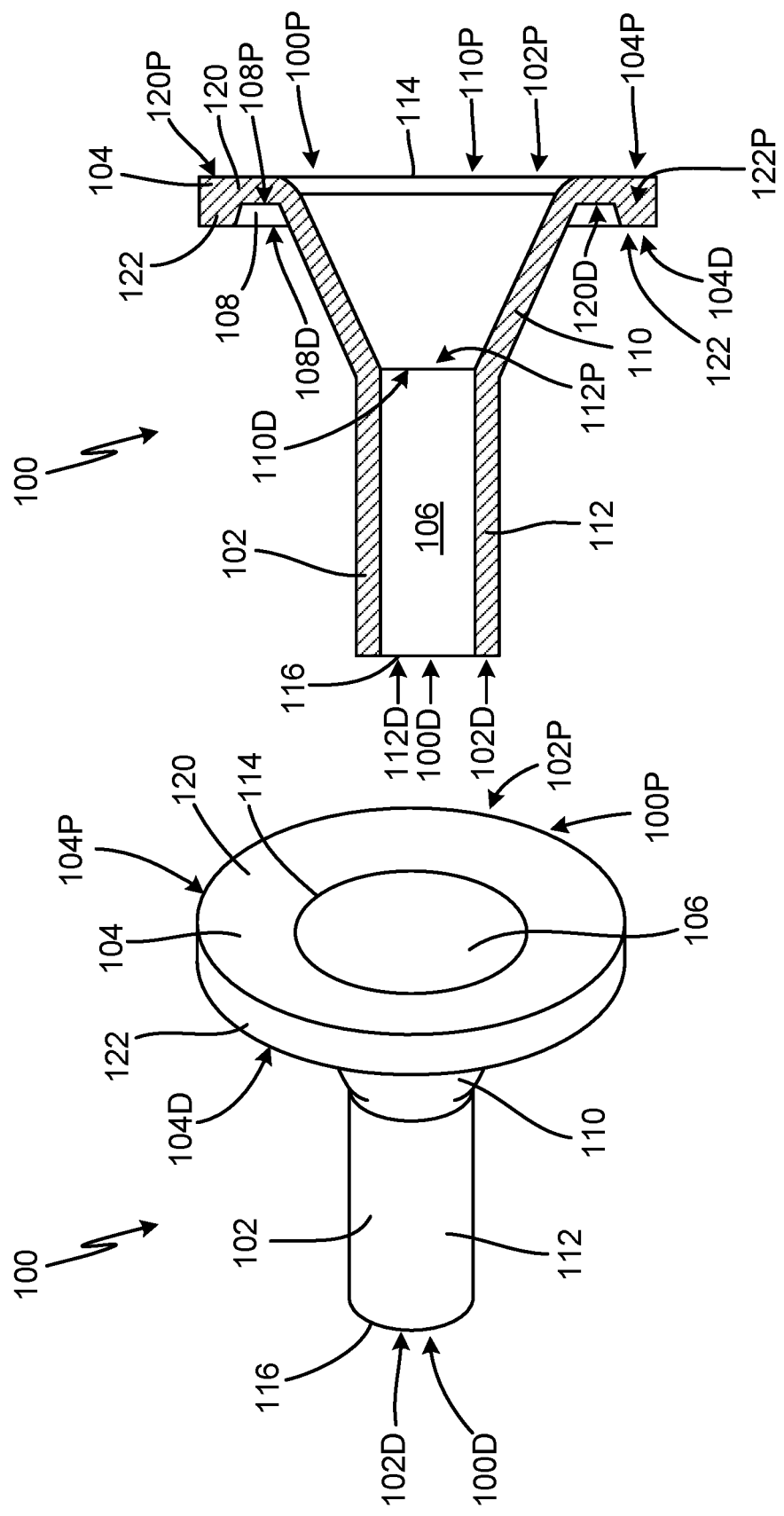

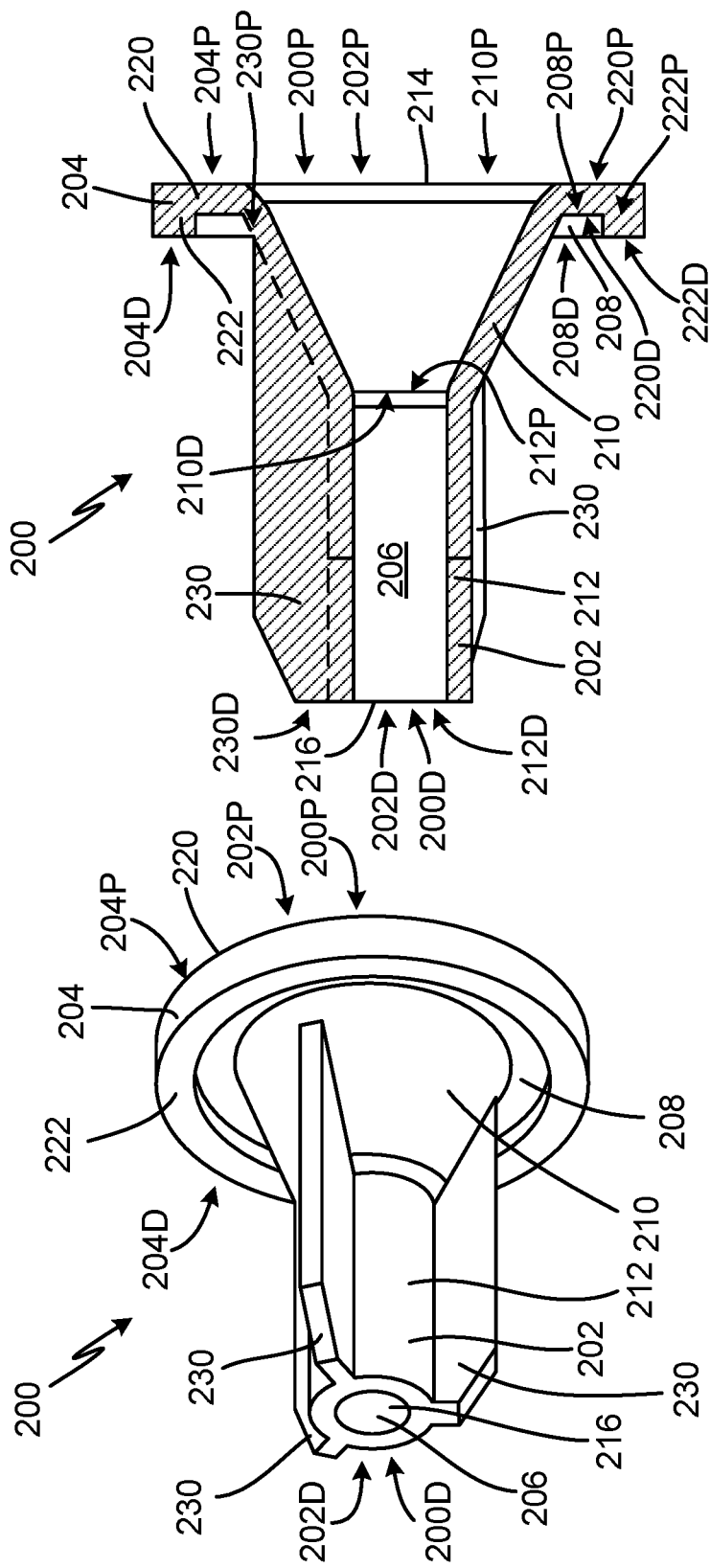

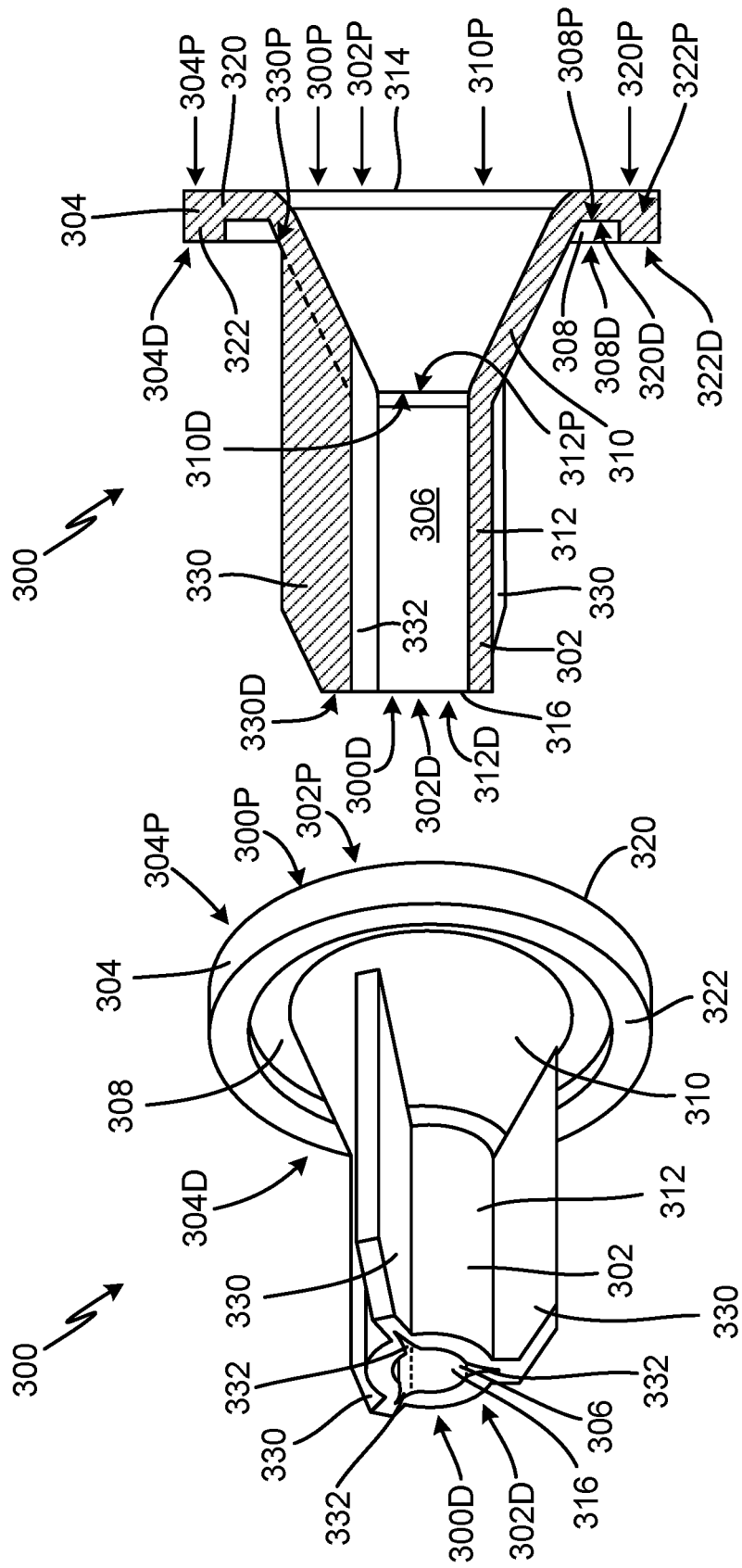

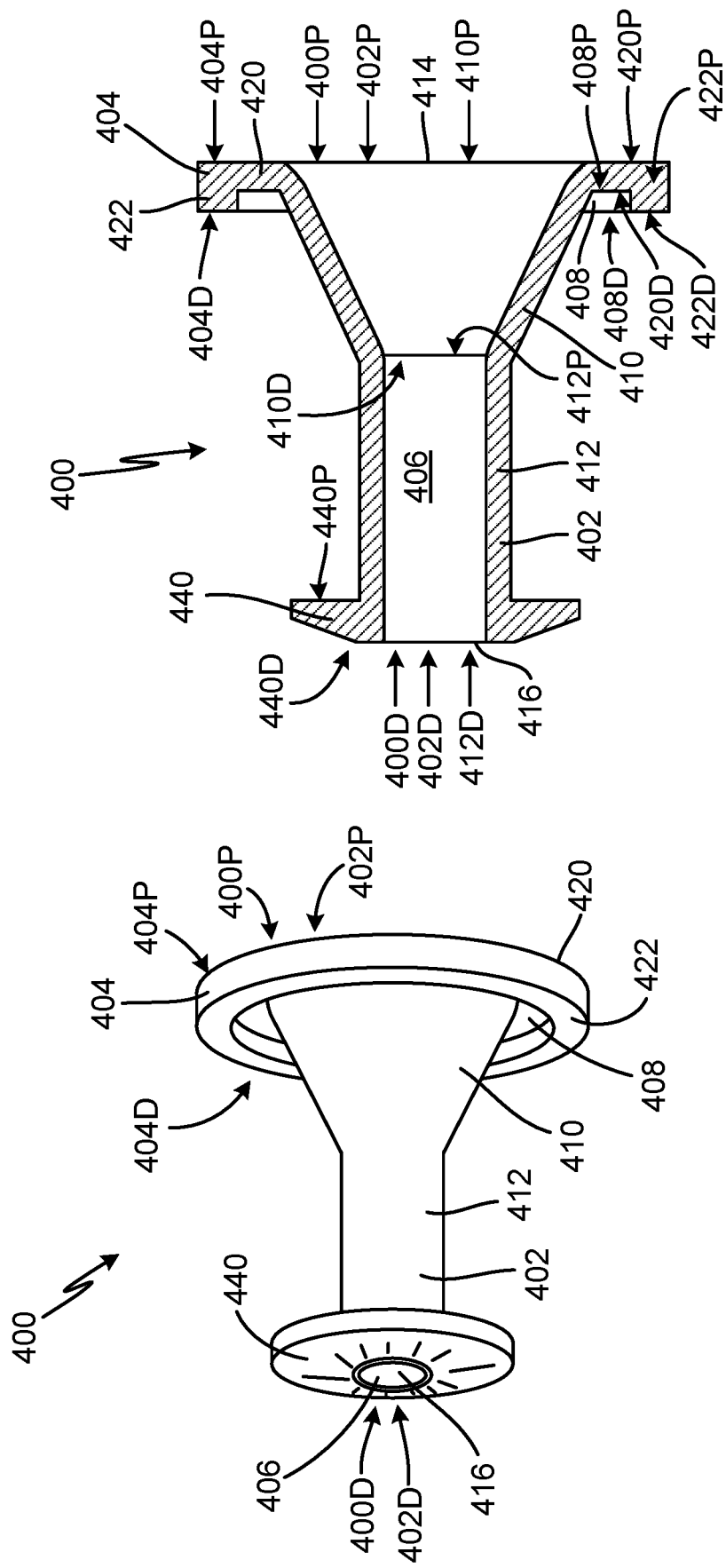

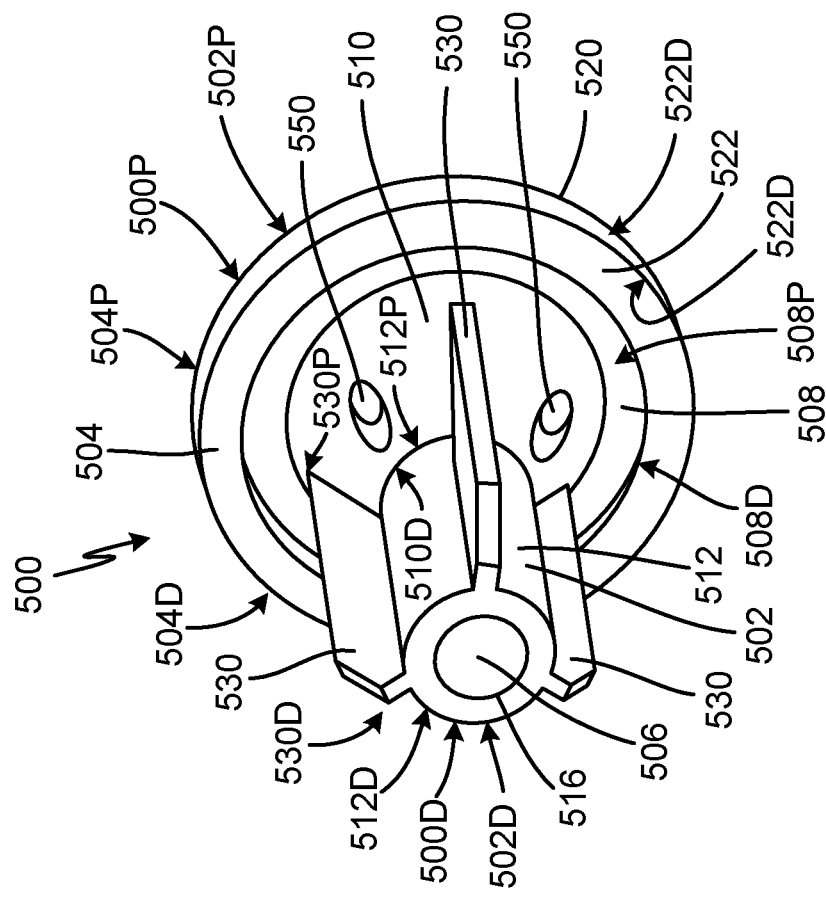
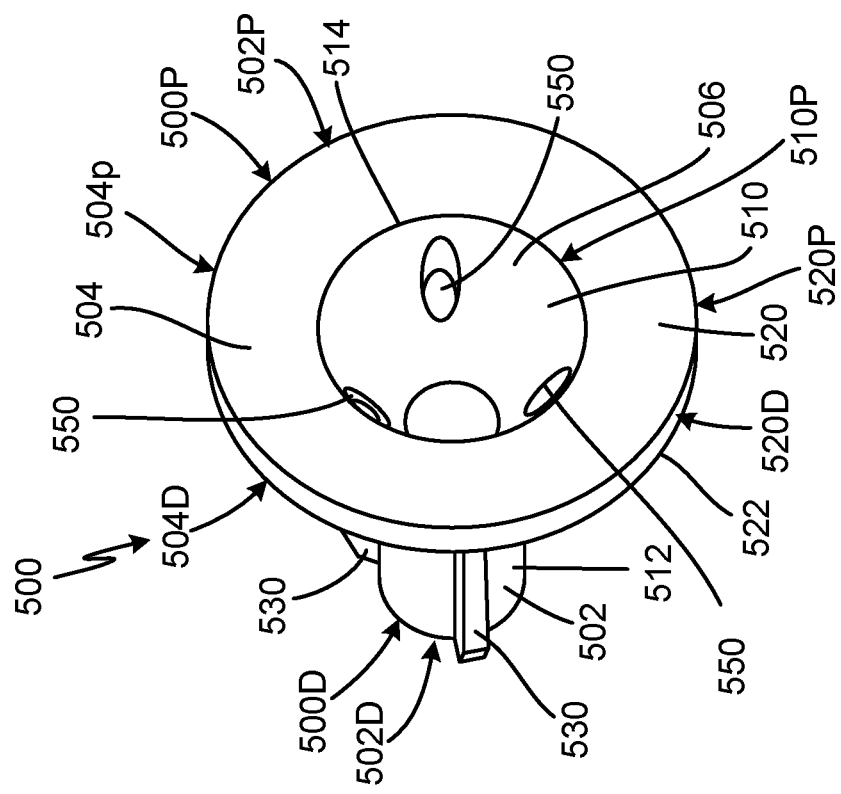
Fig. 11B
Fig. 11A

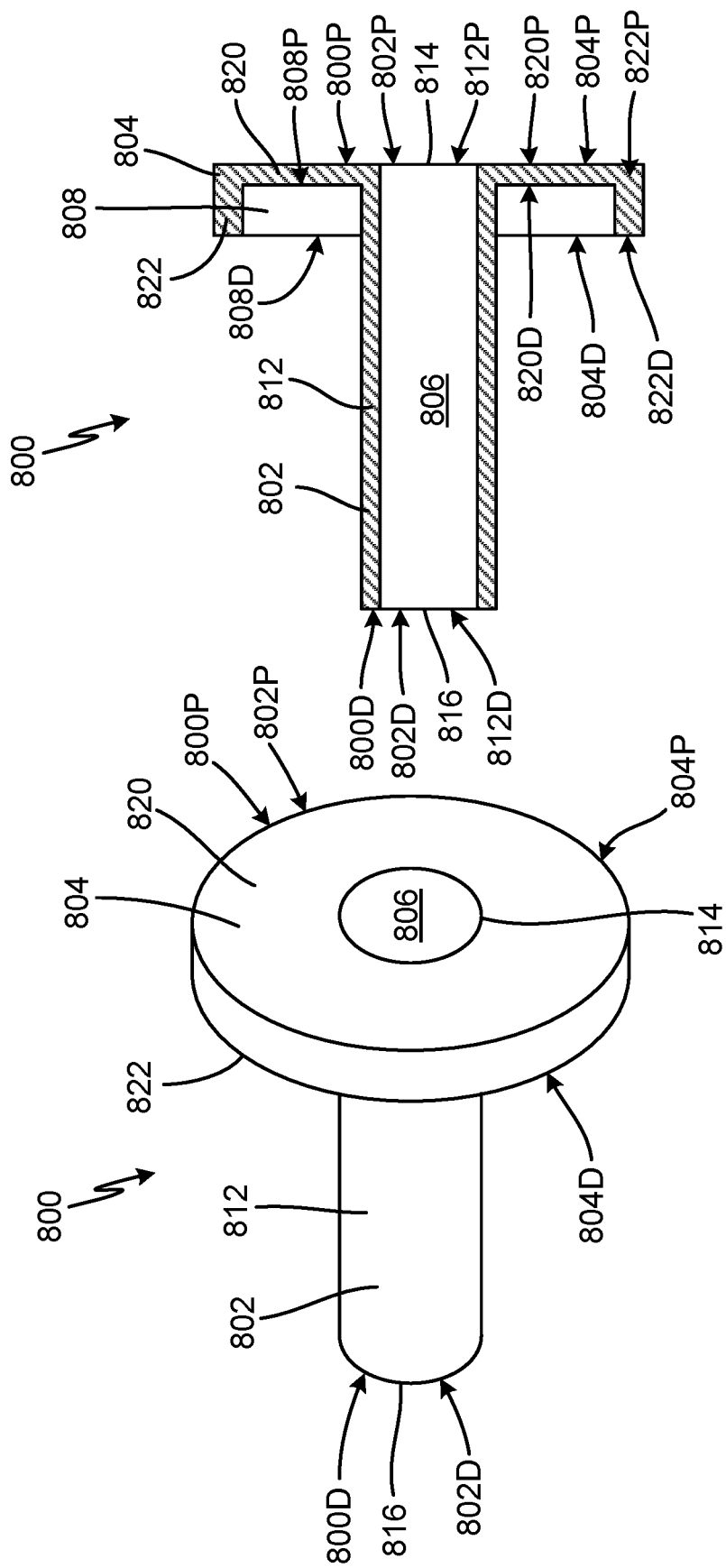

NEEDLE SYSTEM RESTRICTOR

BACKGROUND

The present disclosure relates to a needle system, and in particular, to a restrictor for a needle system.

Endobronchial ultrasound (EBUS) is a diagnostic or staging procedure for lung cancer, lung infections, and other diseases causing enlarged lymph nodes or masses in the chest. EBUS uses an endoscope with ultrasound to visualize the airways, blood vessels, lungs, and lymph nodes in the tracheal and bronchial tree of a patient. Trans-bronchial needle aspiration (TBNA) can be used to perform a biopsy of lesions or lymph nodes within the tracheal and bronchial tree. Endobronchial ultrasound trans-bronchial needle aspiration (EBUS-TBNA) uses ultrasound to visualize the airways, blood vessels, lungs, and lymph nodes in the tracheal and bronchial tree of a patient to perform a biopsy of lesions or lymph nodes within the tracheal and bronchial tree.

During an EBUS-TBNA procedure, an endoscope is inserted into a patient with the head of the endoscope positioned next to a lesion or lymph node from which a sample is to be taken. The endoscope includes a channel through which a needle system can be guided. The needle system includes a sheath connected to a handle. A needle is positioned in the sheath and connected to a needle slider. The needle slider is partially positioned in and movable in the handle. The needle slider can be moved from a retracted position where the needle is held in the sheath to an advanced position where the needle is advanced out of the sheath. In the advanced position, the needle can puncture the lesion or lymph node from which a biological sample is to be taken. A syringe can be connected to an aspiration port on the needle slider and suction can be applied to the needle system to create a vacuum in the needle system. The needle is then moved backwards and forwards in the lesion or lymph node with the needle slider to aspirate a biological sample from the lesion or lymph node into the needle. The needle system is removed from the endoscope and the biological sample is pushed out of the needle to be used for biopsy analysis.

In some existing needle systems, the vacuum generated by the syringe can draw the collected biological sample from the lesion or lymph node into the syringe. This renders the biological sample unsuitable for biopsy analysis.

SUMMARY

A needle system a handle and a needle slider partially positioned in the handle. The needle slider has an aspiration port at a proximal end of the needle slider. A needle connected to and extending away from the needle slider. A restrictor is disposed in the aspiration port of the needle slider. The restrictor is configured to inhibit passage of a sample through the aspiration port.

A restrictor includes a hollow body with a proximal end having a proximal opening and a distal end having a distal opening. The hollow body is configured to fit into an aspiration port of a needle slider. A rim extends from the proximal end of the body. The rim is configured to form a seal between a syringe and the needle slider at the aspiration port.

A method includes positioning a restrictor in a needle system. The needle system has a handle, a needle slider partially positioned in the handle, a sheath secured in the handle, and a needle secured in the needle slider and extending through the sheath. The needle of the needle slider is advanced out of the sheath and into a sample. A syringe is connected to an aspiration port of the needle slider of the needle system. The sample is aspirated into the needle of the needle system. The sample is inhibited, with the restrictor, from moving into the syringe.

BRIEF DESCRIPTION OF THE DRAWINGS

FIG. 6C is a cross-sectional view of the restrictor in the needle slider with the syringe attached.

FIG. 7A is a perspective view of a first embodiment of the restrictor.

FIG. 7B is a cross-sectional view of the first embodiment of the restrictor.

FIG. 8A is a perspective view of a second embodiment of the restrictor.

FIG. 8B is a cross-sectional view of the second embodiment of the restrictor.

FIG. 9A is a perspective view of a third embodiment of the restrictor.

FIG. 9B is a cross-sectional view of the third embodiment of the restrictor.

FIG. 10A is a perspective view of a fourth embodiment of the restrictor.

FIG. 10B is a cross-sectional view of the fourth embodiment of the restrictor.

FIG. 11A is a perspective view of a proximal end of a fifth embodiment of the restrictor.

FIG. 11B is a perspective view of a distal end of the fifth embodiment of the restrictor.

FIG. 14A is a perspective view of an eighth embodiment of the restrictor.

FIG. 14B is a cross-sectional view of an eighth embodiment of the restrictor.

DETAILED DESCRIPTION

Needle System 20 (FIGS. 1A-5)

Figure 1A:
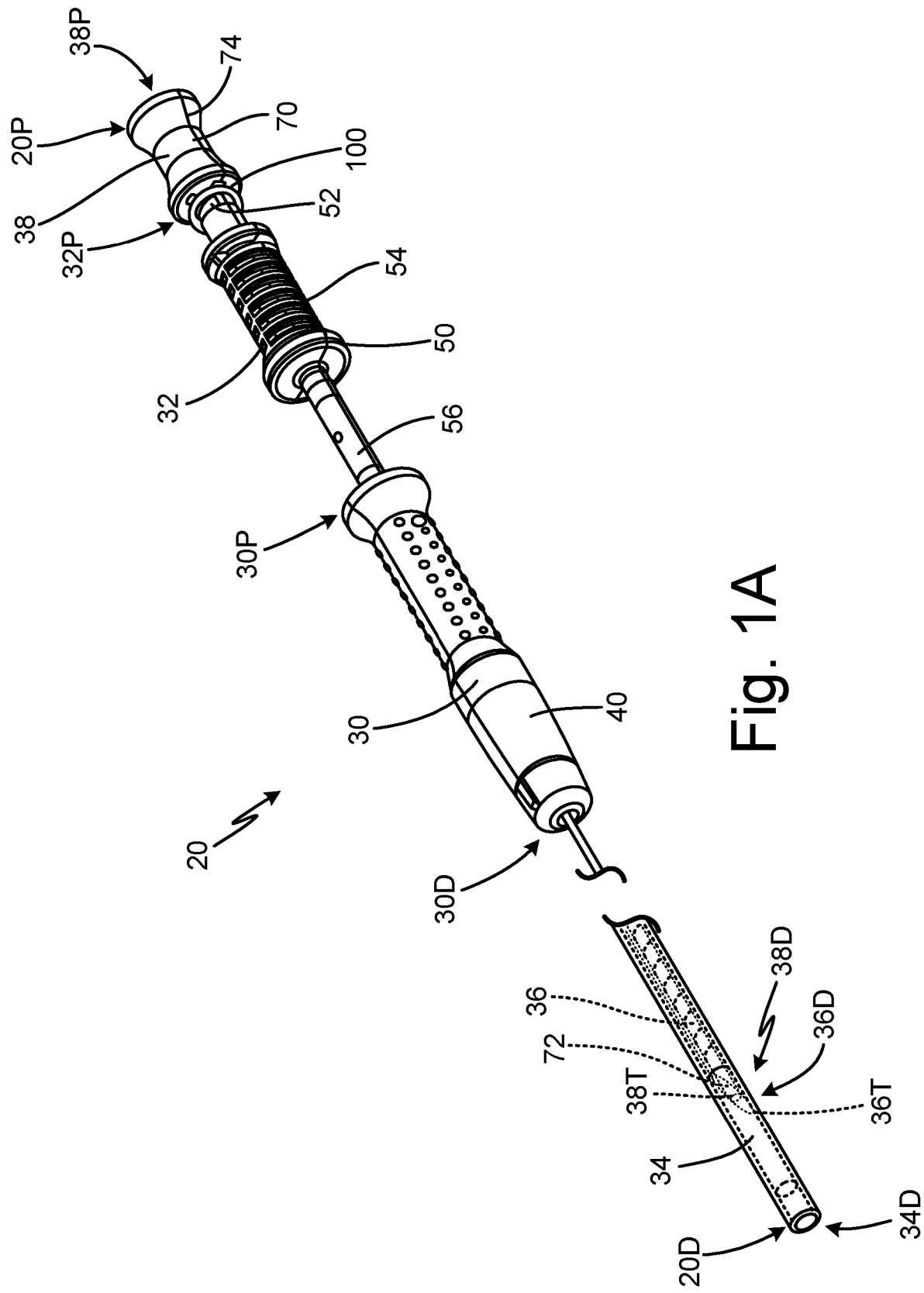
FIG. 1A is an isometric view of a needle system in a retracted position.
Figure 1B:
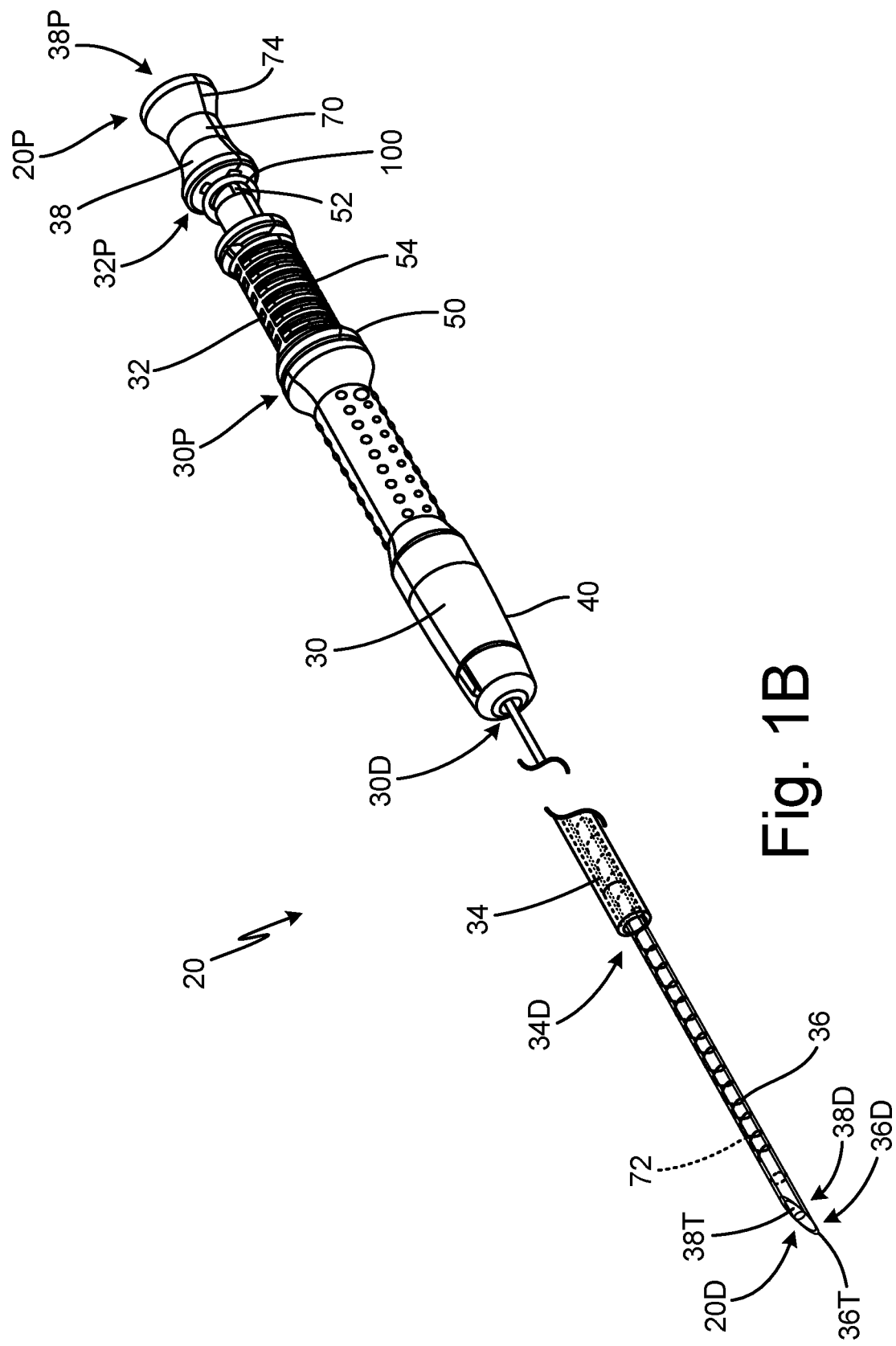
FIG. 1B is an isometric view of the needle system in an advanced position.
Figure 2A:
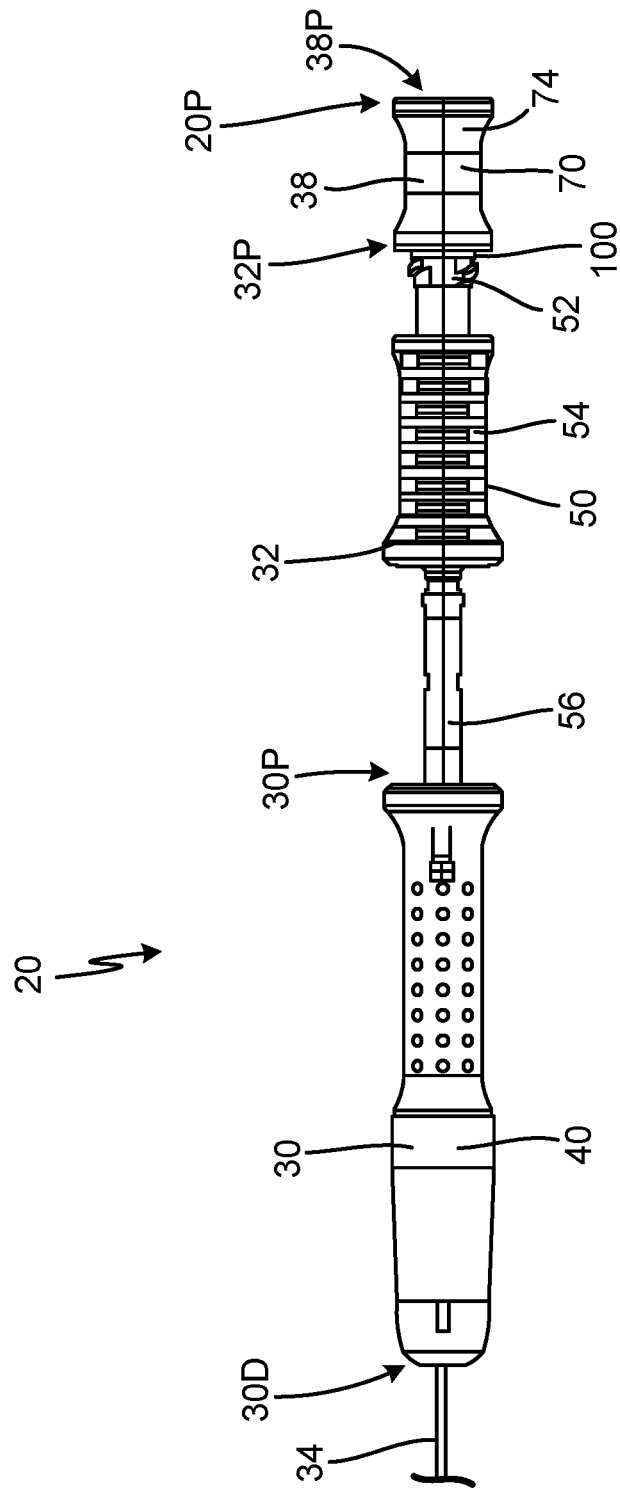
FIG. 2A is a side view of the needle system in the retracted position.
Figure 2B:
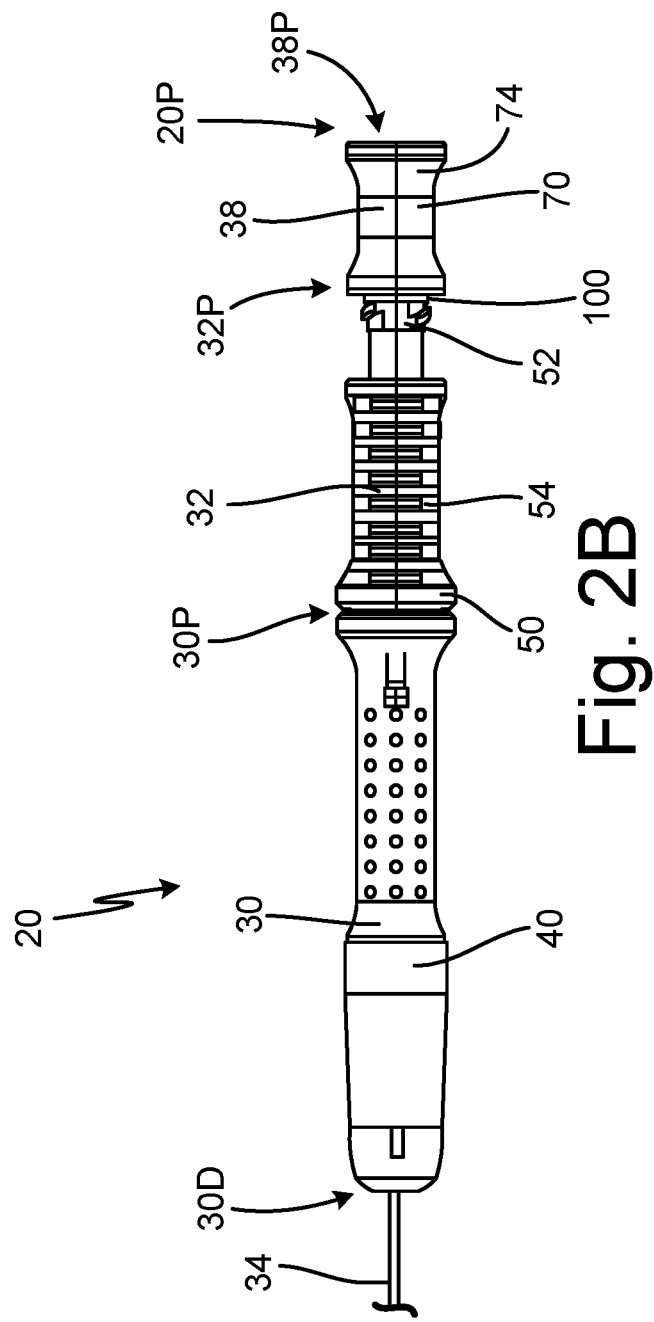
FIG. 2B is a side view of the needle system in the advanced position.
Figure 3:
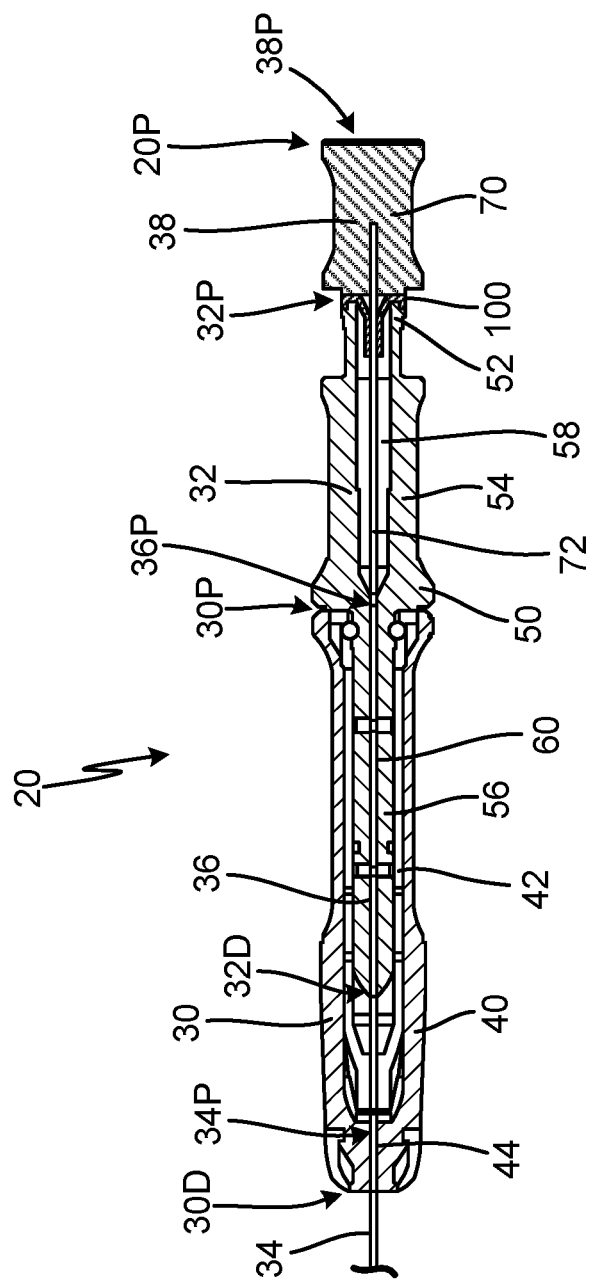
FIG. 3 is a cross-sectional view of the needle system in the advanced position.
Figure 4:
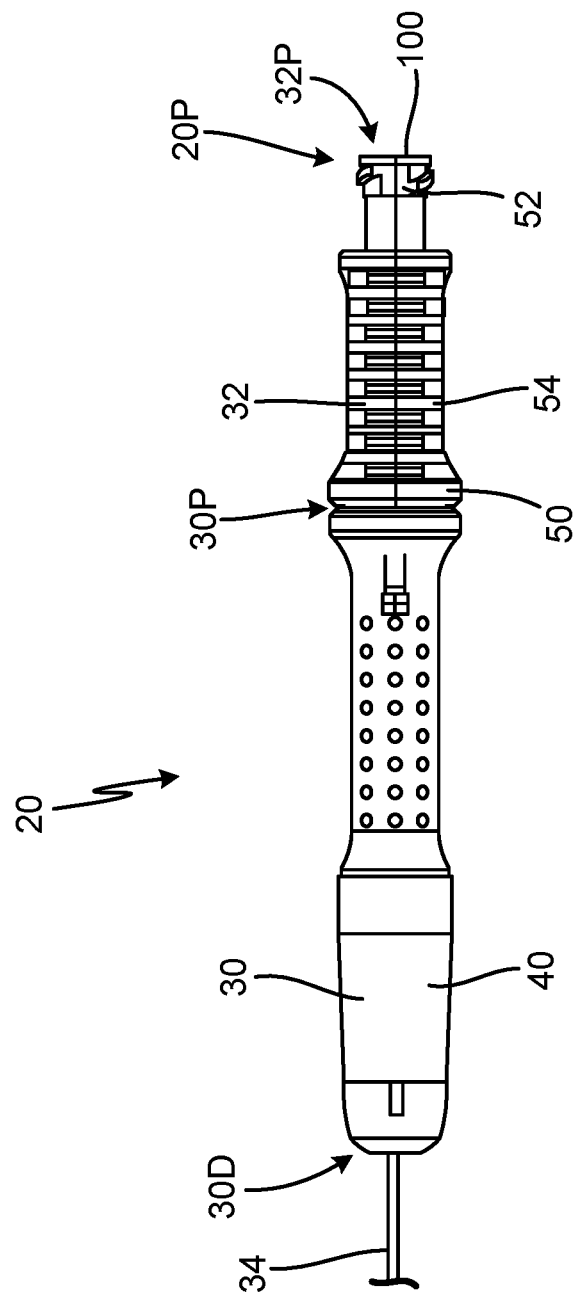
FIG. 4 is a side view of the needle system when a stylet has been removed.
Figure 5:
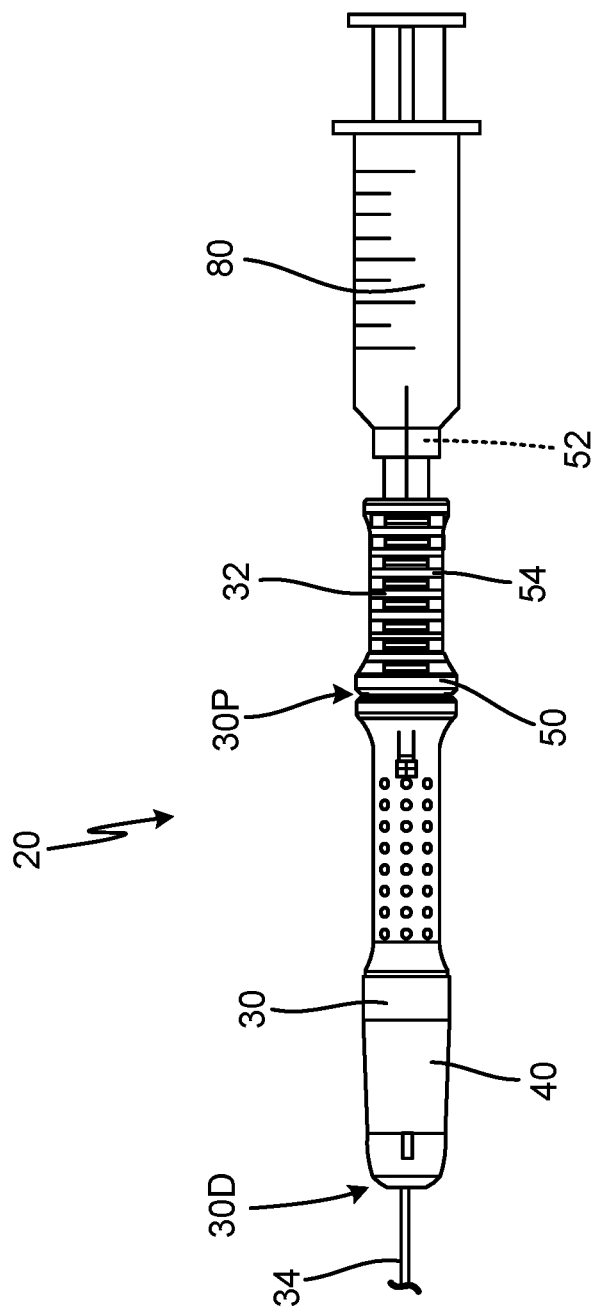
FIG. 5 is a side view of the needle system with a syringe attached.

FIG. 1A is an isometric view of needle system 20 in a retracted position. FIG. 1B is an isometric view of needle system 20 in an advanced position. FIGS. 1A-1B show an enlarged view of distal end 20D of needle system 20 for clarity. FIG. 2A is a side view of needle system 20 in the retracted position. FIG. 2B is a side view of needle system 20 in the advanced position. FIG. 3 is a cross-sectional view of needle system 20 in the advanced position. FIG. 4 is a side view of needle system 20 when stylet 38 has been removed. FIG. 5 is a side view of needle system 20 with syringe 80 attached. FIGS. 2B-5 do not show distal end 20D of needle system 20. FIGS. 1A-5 will be discussed together. Needle system 20 includes handle 30, needle slider 32, sheath 34, needle 36, and stylet 38. Handle 30 includes housing 40, first bore 42, and second bore 44. Needle slider 32 includes housing 50, aspiration port 52, grip 54, shaft 56, first bore 58, and second bore 60. Stylet 38 includes knob 70 and wire 72. FIG. 5 also shows syringe 80, and FIGS. 1A-4 show restrictor 100.

Needle system 20 includes proximal end 20P and distal end 20D. Needle system 20 includes handle 30 forming a body portion that can be gripped by a user while using needle system 20. Handle 30 includes proximal end 30P and distal end 30D. Needle slider 32 is partially positioned in and movable within handle 30. Needle slider 32 includes proximal end 32P and distal end 32D (FIG. 3). Sheath 34 is connected to distal end 30D of handle 30 and extends axially away from handle 30. Sheath 34 includes proximal end 34P (FIG. 3) and distal end 34D. Needle 36 is connected to distal end 32D of needle slider 32 and extends axially away from needle slider 32. Needle 36 includes proximal end 36P (FIG. 3), distal end 36D, and tip 36T. Needle 36 extends through and is coaxial with sheath 34. Stylet 38 is positioned at proximal end 32P of needle slider 32 and extends through needle slider 32 and needle 36. Stylet 38 includes proximal end 38P, distal end 38D, and tip 38T.

Needle system 20 can be moved between a retracted position and an advanced position via manual actuation of needle slider 32. Needle system 20 is shown in the retracted position in FIGS. 1A and 2A. In the retracted position, tip 36T of needle 36 is positioned within distal end 34D of sheath 34. Needle system 20 is shown in the advanced position in FIGS. 1B and 2B-5. In the advanced position, tip 36T of needle 36 is positioned outside of sheath 34 beyond distal end 34D of sheath 34. Needle system 20 is moved between the retracted position and the advanced position by moving needle slider 32 into and out of handle 30. As needle slider 32 is pushed into handle 30, the tip of needle 36 is advanced outside of sheath 34. As needle slider 32 is pulled out of handle 30, the tip of needle 36 is retracted into sheath 34.

As shown in FIG. 3, handle 30 includes housing 40 that forms the body of handle 30. Handle 30 also includes first bore 42 and second bore 44. First bore 42 extends through proximal end 30P of handle 30. First bore 42 is cylindrically shaped in the embodiment shown, but can have any suitable shape in alternate embodiments. Second bore 44 extends through distal end 30D of handle 30. Second bore 44 is cylindrically shaped in the embodiment shown, but can have any suitable shape in alternate embodiments. First bore 42 has a diameter that is greater than a diameter of second bore 44.

Housing 50, which includes aspiration port 52, grip 54, and shaft 56, forms the body of needle slider 32. Aspiration port 52 is situated at proximal end 32P of needle slider 32, grip 54 is situated between aspiration port 52 and shaft 56, and shaft 56 is situated at distal end 32D of needle slider 32. Needle slider 32 includes first bore 58 and second bore 60. First bore 58 extends through aspiration port 52 and grip 54 of needle slider 32. First bore 58 is cylindrically shaped in the embodiment shown, but can have any suitable shape in alternate embodiments. Second bore 60 extends through shaft 56 of needle slider 32. Second bore 60 is cylindrically shaped in the embodiment shown, but can have any suitable shape in alternate embodiments. First bore 58 has a diameter that is greater than a diameter of second bore 60.

Shaft 56 of needle slider 32 is positioned in and movable in first bore 42 of handle 30. As shown in FIGS. 1A and 2A, when needle system 20 is in a retracted position, a majority of shaft 56 of needle slider 32 will not be positioned in first bore 42 of handle 30. As shown in FIGS. 1B and 2B-5, when needle system 20 is in an advanced position, the entirety of shaft 56 of needle slider 32 is positioned in first bore 42 of handle 30.

Sheath 34 is a tube that extends away from distal end 30D of handle 30. Sheath 34 is made of a polymeric material in the embodiment shown. In alternate embodiments, sheath 34 can be made of other suitable materials. Proximal end 34P of sheath 34 is positioned in and secured in second bore 44 of handle 30. Needle 36 is a tube that extends away from distal end 32D of needle slider 32. Needle 36 has tip 36T on distal end 36D. Needle 36 is made of a metal, such as stainless steel, in the embodiment shown. In alternate embodiments, needle 36 can be made of other suitable materials. Proximal end 36P of needle 36 is positioned in and secured in second bore 60 of needle slider 32.

Stylet 38 includes knob 70 and wire 72. Knob 70 forms a body of stylet 38. Knob 70 abuts aspiration port 52 of needle slider 32. Wire 72 is positioned in and extends away from knob 70. Wire 72 extends through first bore 58 and second bore 60 of needle slider 32 and through needle 36. Wire 72 of stylet 38 is coaxial with needle 36. Tip 38T of stylet 38 is positioned in tip 36T of needle 36 when stylet 38 is positioned in needle system 20. Stylet 38 can be removed from needle system 20 by pulling knob 70 away from needle slider 32 and pulling wire 72 out of needle system 20.

Needle system 20 can be used as a single-use aspiration needle for taking biopsies. For example, needle system 20 can be used during trans-bronchial needle aspiration (TBNA) to perform a biopsy of a lesion or a lymph node in the tracheal and bronchial tree of a patient. More specifically, needle system 20 can be used during endobronchial ultrasound trans-bronchial needle aspiration (EBUS-TBNA). During an EBUS-TBNA procedure, an endoscope with ultrasound capabilities is used to visualize the airways, blood vessels, lungs, and lymph nodes in the tracheal and bronchial tree.

Once the endoscope is positioned adjacent to a lesion or a lymph node from which a biological sample is to be collected, sheath 34 of needle system 20 can be inserted through a channel in the endoscope. Handle 30 can be grasped by a user and used to maneuver sheath 34 into position in the endoscope. Needle 36 and wire 72 of stylet 38 provide structural support to sheath 34 as it is inserted into the endoscope, while also allowing sheath 34 to remain flexible. Needle system 20 is in a retracted position, as shown in FIGS. 1A and 2A, when sheath 34 is inserted through the endoscope to ensure that tip 36T of needle 36 does not puncture the endoscope.

After sheath 34 of needle system 20 is inserted into the endoscope, needle system 20 is moved to an advanced position, as shown in FIGS. 1B and 2B-5. Needle slider 32 is pushed into handle 30 of needle system 20 to advance the tip of needle 36 into the target lesion or lymph node. Stylet 38 is then removed from needle system 20, as shown in FIG. 4. When stylet 38 is removed, aspiration port 52 of needle slider 32 forms proximal end 20P of needle system 20, and first bore 58 of needle slider 32 is exposed.

Syringe 80 is attached to proximal end 32P of needle slider 32, as shown in FIG. 5. Syringe 80 has luer fittings that mate to luer fittings on proximal end 32P of needle slider 32. Syringe 80 is used to create a vacuum in needle system 20. First bore 58 of needle slider 32, second bore 60 of needle slider 32, and a lumen of needle 36 form a flow path through needle system 20. A plunger of syringe 80 is pulled to apply suction to needle system 20, creating a vacuum in the flow path extending through first bore 58 of needle slider 32, second bore 60 of needle slider 32, and a lumen of needle 36.

After a vacuum has been applied with syringe 80, needle slider 32 is moved into and out of handle 30, moving the tip of needle 36 backwards and forwards within the lesion or lymph node. A biological sample from the lesion or lymph node will be aspirated into needle 36 via the vacuum supplied by syringe 80 and the movement of needle slider 32. The biological sample that is aspirated into needle system 20 is drawn under suction into the lumen of needle 36, second bore 60 of needle slider 32, and first bore 58 of needle slider 32. After a biological sample has been aspirated into needle 36, syringe 80 is removed from proximal end 32P of needle slider 32. Needle system 20 is then removed from the endoscope and the biological sample is removed from needle 36 for biopsy analysis.

One challenge that is faced in using needle system 20 is preventing the aspirated biological sample from entering syringe 80. If the biological sample enters syringe 80, it is unsuitable for use in a biopsy analysis. This would require a second needle system 20 to be inserted into the endoscope to collect a new sample for conducting the biopsy analysis. Restrictor 100 is positioned in aspiration port 52 of needle slider 32 to prevent biological material from being drawn into syringe 80. Restrictor 100 can be seen in FIGS. 1A-4. Restrictor 100 is made of a flexible material so that it can deform when stylet 38 is positioned in needle slider 32, as shown in FIG. 3.

As will be discussed below with reference to FIGS. 6A-12B, in its natural state, restrictor 100 will have a smaller diameter than a diameter of first bore 58 of needle slider 32. This reduced diameter will inhibit the biological material from moving through restrictor 100 and into syringe 80. Restrictor acts as an internal nozzle and/or phase separator, as it allows fluid to pass through (thus allowing syringe 80 to create a vacuum in needle system 20) but inhibits solid material to pass through (the aspirated biological sample).

Restrictor 100 (FIGS. 6A-7B)

Figure 6A:
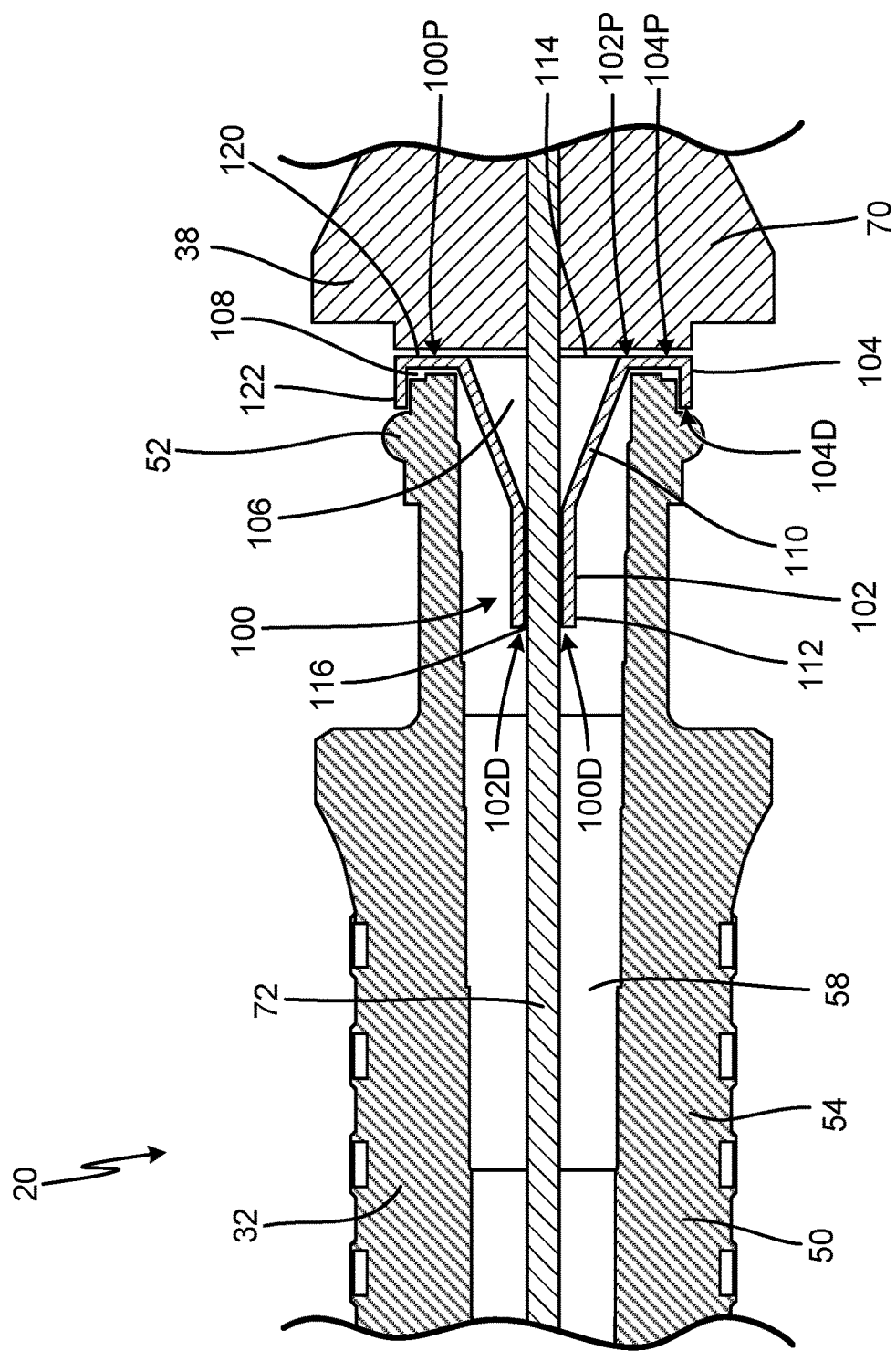
FIG. 6A is a cross-sectional view of a restrictor in a needle slider when the stylet is fully positioned in the needle system.
Figure 6B:
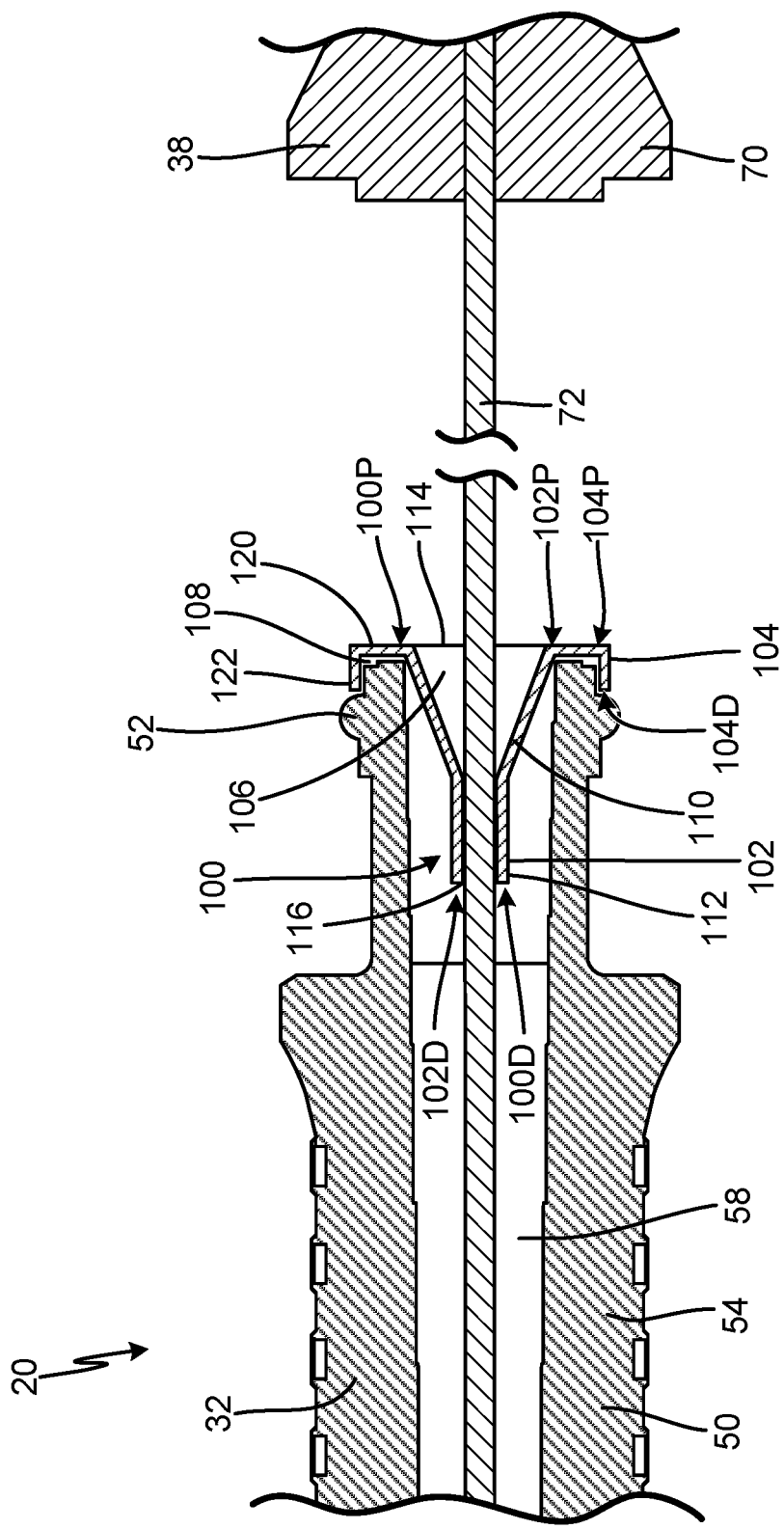
FIG. 6B is a cross-sectional view of the restrictor in the needle slider when the stylet is partially positioned in the needle system.

FIG. 6A is a cross-sectional view of restrictor 100 in needle slider 32 when stylet 38 is fully positioned in needle system 20. FIG. 6B is a cross-sectional view of restrictor 100 in needle slider 32 when stylet 38 is partially positioned in needle system 20. FIG. 6C is a cross-sectional view of restrictor 100 in needle slider 32 with syringe 80 attached. FIG. 7A is a perspective view of restrictor 100. FIG. 7B is a cross-sectional view of restrictor 100. FIGS. 6A-6C shows needle slider 32, housing 50, aspiration port 52, grip 54, and first bore 58 of needle system 20. FIGS. 6A-6B also show stylet 38, including knob 70 and wire 72. FIG. 6C also shows syringe 80. FIGS. 6A-7B show restrictor 100. Restrictor 100 includes body 102, rim 104, interior 106, and groove 108. Body 102 includes frustoconical portion 110, cylindrical portion 112, proximal opening 114, and distal opening 116. Rim 104 includes flange portion 120 and lip portion 122.

Needle slider 32 has the structure as described in reference to FIGS. 1A-5 above. Syringe 80 is connected to aspiration port 52 of needle slider 32 with luer fittings. Restrictor 100 is disposed in aspiration port 52 of needle slider 32 of needle system 20. Restrictor 100 is described for use with needle system 20 shown in FIGS. 1A-6C, but restrictor 100 can be used with any needle system in alternate embodiments. FIGS. 1A-6C show restrictor 100 as being disposed in needle system 20 when stylet 38 is positioned in needle system 20. In an alternate embodiment, restrictor 100 can be positioned in needle system 20 after stylet 38 has been removed.

Restrictor 100 has proximal end 100P and distal end 100D. Restrictor 100 includes body 102 and rim 104. Body 102 extends from proximal end 100P to distal end 100D of restrictor 100. Body 102 has proximal end 102P and distal end 102D. Rim 104 extends radially outward from proximal end 102P of body 102. Rim 104 has proximal end 104P and distal end 104D. Body 102 and rim 104 are integrally formed in the embodiment shown in FIGS. 6A-7B. In an alternate embodiment, body 102 and rim 104 can be two pieces that are connected together. Body 102 is hollow and has interior 106 extending from proximal end 102P to distal end 102D of body 102. Groove 108 is defined between body 102 and rim 104. Groove 108 has proximal end 108P and distal end 108D.

Body 102 of restrictor 100 includes frustoconical portion 110 and cylindrical portion 112. Frustoconical portion 110 forms proximal end 102P of body 102 and cylindrical portion 112 forms distal end 102D of body 102. Frustoconical portion 110 has proximal end 110P and distal end 110D, and cylindrical portion 112 has proximal end 112P and distal end 112D. Proximal end 110P of frustoconical portion 110 is aligned with proximal end 100P of restrictor 100, and distal end 112D of cylindrical portion 112 is aligned with distal end 100D of restrictor 100. Distal end 110D of frustoconical portion 110 is connected to proximal end 112P of cylindrical portion 112. Frustoconical portion 110 has a greater diameter at proximal end 110P and tapers to a smaller diameter at distal end 110D. Cylindrical portion 112 has a constant diameter from proximal end 112P to distal end 112D. The diameter of distal end 110D of frustoconical portion 110 is the same as the diameter of cylindrical portion 112. Proximal opening 114 is formed at proximal end 102P of body 102, and distal opening 116 is formed at distal end 102D of body 102. Proximal opening 114 has a greater diameter than a diameter of distal opening 116.

Rim 104 includes flange portion 120 and lip portion 122. Flange portion 120 extends radially outward from proximal end 110P of frustoconical portion 110 of body 102. Flange portion 120 is shaped like a flat ring. Flange portion 120 includes proximal end 120P and distal end 120D. A radially inner surface of rim 104 is connected to a radially outer surface of frustoconical portion 110 of body 102. Proximal end 120P of flange portion 120 is aligned with proximal end 104P of rim 104 and proximal end 100P of restrictor 100. Lip portion 122 is circumferential and extends in an axial direction away from distal end 120D of flange portion 120. Lip portion 122 includes proximal end 122P and distal end 122D. Lip portion 122 is shaped like a cylinder. Proximal end 122P of lip portion 122 is connected to distal end 120D of flange portion 120. Distal end 122D of lip portion 122 is aligned with distal end 104D of rim 104.

Interior 106 extends through frustoconical portion 110 and cylindrical portion 112 of body 102. A radially inner surface of frustoconical portion 110 and cylindrical portion 112 of body 102 form interior 106. Groove 108 is formed between frustoconical portion 110 of body 102, flange portion 120 of rim 104, and lip portion 122 of rim 104. Groove 108 is shaped like a ring. A radially outer surface of frustoconical portion 110 of body 102 defines a radially inner surface of groove 108; distal end 120D of flange portion 120 of rim 104 defines proximal end 108P of groove 108; and a radially inner surface of lip portion 122 of rim 104 defines a radially outer surface of groove 108. Distal end 108D of groove 108 is open.

Restrictor 100 is disposed in needle system 20 so that body 102 of restrictor 100 is disposed in first bore 58 of needle slider 32 and rim 104 of restrictor 100 sits around proximal end 132P of aspiration port 132. Proximal end 132P of aspiration port 132 thus sits in groove 108 of restrictor 100.

Restrictor 100 is made of a flexible material, so that it is capable of being deformed. Restrictor 100 is made of a polymer, such as silicon rubber, plasticized polyvinyl chloride (PVC), or urethane, in the embodiment shows, but can be any suitable material in alternate embodiments. Cylindrical portion 112 of body 102 and distal end 110D of frustoconical portion 110 of body 102 can have a diameter that is smaller than a diameter of wire 72 of stylet 38. When stylet 38 is fully disposed in needle system 20, restrictor 100 is deformed as cylindrical portion 112 of body 102 and distal end 110D of frustoconical portion 110 of body 102 are pushed outwards with wire 72 of stylet 38, as shown in FIG. 6A. This allows both stylet 38 and restrictor 100 to be disposed in needle system 20 at the same time. Cylindrical portion 112 of body 102 and distal end 110D of frustoconical portion 110 of body 102 will remain deformed as stylet 38 is removed from needle system 20, as shown in FIG. 6B. After stylet 38 is fully removed from needle system 20, restrictor 100 will resume its natural state and a flow path will extend through restrictor 100. In an alternate embodiment, cylindrical portion 112 of body 102 and distal end 110D of frustoconical portion 110 of body 102 can have the same or a slightly larger diameter than wire 72 of stylet 38. Further, when syringe 80 is attached to aspiration port 52 of needle slider 32, restrictor 100 is secured between and a seal is formed between aspiration port 52 of needle slider 32 and syringe 80, as shown in FIG. 6C.

Interior 106 of restrictor 100 is aligned with and coaxial with first bore 58 of needle slider 32. Fluid can flow through interior 106 of body 102 of restrictor 100 between syringe 80 and needle system 20. This allows a vacuum to be created in needle system 20 using syringe 80. The vacuum in needle system 20 helps to aspirate a biological sample into needle system 20. Distal opening 116 of body 102 of restrictor 100 has a diameter than is smaller than the diameter of first bore 58 of needle slider 32. The small size of distal opening 116 of body 102 of restrictor 100 compared to first bore 58 of needle slider 32 inhibits solid material, such as the biological sample that is aspirated into needle system 20, from entering restrictor 100. Thus, solid material, such as the biological sample that is aspirated into needle system 20, is inhibited from being drawn into syringe 80.

Restrictor 100 is a first embodiment of a restrictor. FIGS. 8A-12B describe further embodiments of a restrictor. The various embodiments of restrictors described below can each be used with needle system 20 described in FIGS. 1A-6 or with other needle systems.

Restrictor 200 (FIGS. 8A-8B)

FIG. 8A is a perspective view of restrictor 200. FIG. 8B is a cross-sectional view of restrictor 200. Restrictor 200 includes body 202, rim 204, opening 206, and groove 208. Body 202 includes frustoconical portion 210, cylindrical portion 212, proximal opening 214, and distal opening 216. Rim 204 includes flange portion 220 and lip portion 222. Restrictor 200 further includes ribs 230.

Restrictor 200 has proximal end 200P and distal end 200D. Restrictor 200 includes body 202 and rim 204. Body 202 extends from proximal end 200P to distal end 200D of restrictor 200. Body 202 has proximal end 202P and distal end 202D. Rim 204 extends radially outward from proximal end 202P of body 202. Rim 204 has proximal end 204P and distal end 204D. Body 202 and rim 204 are integrally formed in the embodiment shown in FIGS. 8A-8B. In an alternate embodiment, body 202 and rim 204 can be two pieces that are connected together. Body 202 is hollow and has interior 206 extending from proximal end 202P to distal end 202D of body 202. Groove 208 is defined between body 202 and rim 204. Groove 208 has proximal end 208P and distal end 208D.

Body 202 of restrictor 200 includes frustoconical portion 210 and cylindrical portion 212. Frustoconical portion 210 forms proximal end 202P of body 202 and cylindrical portion 212 forms distal end 202D of body 202. Frustoconical portion 210 has proximal end 210P and distal end 210D, and cylindrical portion 212 has proximal end 212P and distal end 212D. Proximal end 210P of frustoconical portion 210 is aligned with proximal end 200P of restrictor 200, and distal end 212D of cylindrical portion 212 is aligned with distal end 200D of restrictor 200. Distal end 210D of frustoconical portion 210 is connected to proximal end 212P of cylindrical portion 212. Frustoconical portion 210 has a greater diameter at proximal end 210P and tapers to a smaller diameter at distal end 210D. Cylindrical portion 212 has a constant diameter from proximal end 212P to distal end 212D. The diameter of distal end 210D of frustoconical portion 210 is the same as the diameter of cylindrical portion 212. Proximal opening 214 is formed at proximal end 202P of body 202, and distal opening 216 is formed at distal end 202D of body 202. Proximal opening 214 has a greater diameter than a diameter of distal opening 216.

Rim 204 includes flange portion 220 and lip portion 222. Flange portion 220 extends radially outward from proximal end 210P of frustoconical portion 210 of body 202. Flange portion 220 is shaped like a flat ring. Flange portion 220 includes proximal end 220P and distal end 220D. A radially inner surface of rim 204 is connected to a radially outer surface of frustoconical portion 210 of body 202. Proximal end 220P of flange portion 220 is aligned with proximal end 204P of rim 204 and proximal end 200P of restrictor 200. Lip portion 222 is circumferential and extends in an axial direction away from distal end 220D of flange portion 220. Lip portion 222 includes proximal end 222P and distal end 222D. Lip portion 222 is shaped like a cylinder. Proximal end 222P of lip portion 222 is connected to distal end 220D of flange portion 220. Distal end 222D of lip portion 222 is aligned with distal end 204D of rim 204.

Interior 206 extends through frustoconical portion 210 and cylindrical portion 212 of body 202. A radially inner surface of frustoconical portion 210 and cylindrical portion 212 of body 202 form interior 206. Groove 208 is formed between frustoconical portion 210 of body 202, flange portion 220 of rim 204, and lip portion 222 of rim 204. Groove 208 is shaped like a ring. A radially outer surface of frustoconical portion 210 of body 202 defines a radially inner surface of groove 208; distal end 220D of flange portion 220 of rim 204 defines proximal end 208P of groove 208; and a radially inner surface of lip portion 222 of rim 204 defines a radially outer surface of groove 208. Distal end 208D of groove 208 is open.

Ribs 230 are positioned on restrictor 200. Ribs 230 extend radially outward from body 202 of restrictor 200. There are three ribs 230 positioned on body 202 in the embodiment shown in FIGS. 8A-8B, but any number of ribs 230 can be used in alternate embodiments. Ribs 230 extend along a portion of frustoconical portion 210 of body 202 and along cylindrical portion 212 of body 202. Ribs 230 each have a radially inner edge and a radially outer edge. The radially inner edge has a first portion that is beveled and connected to frustoconical portion 210 of body 202 and a second portion that is straight and connected to cylindrical portion 212 of body 202. The radially outer edge has a first portion that is straight that extends from proximal end 2020P of body 202 and a second portion that beveled extending from the first portion to distal end 202D of body 202.

Restrictor 200 is made of a flexible material, so that it is capable of being deformed. Restrictor 200 is made of a polymer, such as silicon rubber, plasticized polyvinyl chloride (PVC), or urethane, in the embodiment shows, but can be any suitable material in alternate embodiments. Cylindrical portion 212 of body 202 and distal end 210D of frustoconical portion 210 of body 202 can have a diameter that is smaller than a diameter of wire 72 of stylet 38. When stylet 38 is disposed in needle system 20, restrictor 200 is deformed as cylindrical portion 212 of body 202 and distal end 210D of frustoconical portion 210 of body 202 are pushed outwards. This allows both stylet 38 and restrictor 200 to be disposed in needle system 20 at the same time. When stylet 38 is removed, restrictor 200 will resume its natural state. In an alternate embodiment, cylindrical portion 212 of body 202 and distal end 210D of frustoconical portion 210 of body 202 can have the same or a slightly larger diameter than wire 72 of stylet 38. Further, when syringe 80 is attached to aspiration port 52 of needle slider 32, restrictor 200 is secured between and a seal is formed between aspiration port 52 of needle slider 32 and syringe 80.

Interior 206 of restrictor 200 is aligned with and coaxial with first bore 58 of needle slider 32. Fluid can flow through interior 206 of body 202 of restrictor 200 between syringe 80 and needle system 20. This allows a vacuum to be created in needle system 20 using syringe 80. The vacuum in needle system 20 helps to aspirate a biological sample into needle system 20. Distal opening 216 of body 202 of restrictor 200 has a diameter than is smaller than the diameter of first bore 58 of needle slider 32. The small size of distal opening 216 of body 202 of restrictor 200 compared to first bore 58 of needle slider 32 inhibits solid material, such as the biological sample that is aspirated into needle system 20, from entering restrictor 200. Thus, solid material, such as the biological sample that is aspirated into needle system 20, is inhibited from being drawn into syringe 80.

Ribs 230 are positioned on restrictor 200 to provide structural support to restrictor 200. Ribs 230 are flexible and can be flattened when stylet 38 is positioned in restrictor 200. Ribs 230 also help to prevent cylindrical portion 212 of body 202 from inverting when stylet 38 is removed from needle system 20 and restrictor 200.

Restrictor 300 (FIGS. 9A-9B)

FIG. 9A is a perspective view of restrictor 300. FIG. 9B is a cross-sectional view of restrictor 300. Restrictor 300 includes body 302, rim 304, opening 306, and groove 308. Body 302 includes frustoconical portion 310, cylindrical portion 312, proximal opening 314, and distal opening 316. Rim 304 includes annulus portion 320 and flange portion 322. Restrictor 300 further includes ribs 330 and slits 332.

Restrictor 300 has proximal end 300P and distal end 300D. Restrictor 300 includes body 302 and rim 304. Body 302 extends from proximal end 300P to distal end 300D of restrictor 300. Body 302 has proximal end 302P and distal end 302D. Rim 304 extends radially outward from proximal end 302P of body 302. Rim 304 has proximal end 304P and distal end 304D. Body 302 and rim 304 are integrally formed in the embodiment shown in FIGS. 9A-9B. In an alternate embodiment, body 302 and rim 304 can be two pieces that are connected together. Body 302 is hollow and has interior 306 extending from proximal end 302P to distal end 302D of body 302. Groove 308 is defined between body 302 and rim 304. Groove 308 has proximal end 308P and distal end 308D.

Body 302 of restrictor 300 includes frustoconical portion 310 and cylindrical portion 312. Frustoconical portion 310 forms proximal end 302P of body 302 and cylindrical portion 312 forms distal end 302D of body 302. Frustoconical portion 310 has proximal end 310P and distal end 310D, and cylindrical portion 312 has proximal end 312P and distal end 312D. Proximal end 310P of frustoconical portion 310 is aligned with proximal end 300P of restrictor 300, and distal end 312D of cylindrical portion 312 is aligned with distal end 300D of restrictor 300. Distal end 310D of frustoconical portion 310 is connected to proximal end 312P of cylindrical portion 312. Frustoconical portion 310 has a greater diameter at proximal end 310P and tapers to a smaller diameter at distal end 310D. Cylindrical portion 312 has a constant diameter from proximal end 312P to distal end 312D. The diameter of distal end 310D of frustoconical portion 310 is the same as the diameter of cylindrical portion 312. Proximal opening 314 is formed at proximal end 302P of body 302, and distal opening 316 is formed at distal end 302D of body 302. Proximal opening 314 has a greater diameter than a diameter of distal opening 316.

Rim 304 includes flange portion 320 and lip portion 322. Flange portion 320 extends radially outward from proximal end 310P of frustoconical portion 310 of body 302. Flange portion 320 is shaped like a flat ring. Flange portion 320 includes proximal end 320P and distal end 320D. A radially inner surface of rim 304 is connected to a radially outer surface of frustoconical portion 310 of body 302. Proximal end 320P of flange portion 320 is aligned with proximal end 304P of rim 304 and proximal end 300P of restrictor 300. Lip portion 322 is circumferential and extends in an axial direction away from distal end 320D of flange portion 320. Lip portion 322 includes proximal end 322P and distal end 322D. Lip portion 322 is shaped like a cylinder. Proximal end 322P of lip portion 322 is connected to distal end 320D of flange portion 320. Distal end 322D of lip portion 322 is aligned with distal end 304D of rim 304.

Interior 306 extends through frustoconical portion 310 and cylindrical portion 312 of body 302. A radially inner surface of frustoconical portion 310 and cylindrical portion 312 of body 302 form interior 306. Groove 308 is formed between frustoconical portion 310 of body 302, flange portion 320 of rim 304, and lip portion 322 of rim 304. Groove 308 is shaped like a ring. A radially outer surface of frustoconical portion 310 of body 302 defines a radially inner surface of groove 308; distal end 320D of flange portion 320 of rim 304 defines proximal end 308P of groove 308; and a radially inner surface of lip portion 322 of rim 304 defines a radially outer surface of groove 308. Distal end 308D of groove 308 is open.

Ribs 330 are positioned on restrictor 300. Ribs 330 extend radially outward from body 302 of restrictor 300. There are three ribs 330 positioned on body 302 in the embodiment shown in FIGS. 9A-9B, but any number of ribs 330 can be used in alternate embodiments. Ribs 330 extend along a portion of frustoconical portion 310 of body 302 and along cylindrical portion 312 of body 302. Ribs 330 each have a radially inner edge and a radially outer edge. The radially inner edge has a first portion that is beveled and connected to frustoconical portion 310 of body 302 and a second portion that is straight and connected to cylindrical portion 312 of body 302. The radially outer edge has a first portion that is straight that extends from proximal end 3020P of body 302 and a second portion that beveled extending from the first portion to distal end 302D of body 302. Restrictor 300 further includes slits 332 extending through body 302 and into ribs 330. Slits 332 are openings cut through body 302 and into an interior of ribs 330.

Restrictor 300 is made of a flexible material, so that it is capable of being deformed. Restrictor 300 is made of a polymer, such as silicon rubber, plasticized polyvinyl chloride (PVC), or urethane, in the embodiment shows, but can be any suitable material in alternate embodiments. Cylindrical portion 312 of body 302 and distal end 310D of frustoconical portion 310 of body 302 can have a diameter that is smaller than a diameter of wire 72 of stylet 38. When stylet 38 is disposed in needle system 20, restrictor 300 is deformed as cylindrical portion 312 of body 302 and distal end 310D of frustoconical portion 310 of body 302 are pushed outwards. This allows both stylet 38 and restrictor 300 to be disposed in needle system 20 at the same time. When stylet 38 is removed, restrictor 300 will resume its natural state. In an alternate embodiment, cylindrical portion 312 of body 302 and distal end 310D of frustoconical portion 310 of body 302 can have the same or a slightly larger diameter than wire 72 of stylet 38. Further, when syringe 80 is attached to aspiration port 52 of needle slider 32, restrictor 300 is secured between and a seal is formed between aspiration port 52 of needle slider 32 and syringe 80.

Interior 306 of restrictor 300 is aligned with and coaxial with first bore 58 of needle slider 32. Fluid can flow through interior 306 of body 302 of restrictor 300 between syringe 80 and needle system 20. This allows a vacuum to be created in needle system 20 using syringe 80. The vacuum in needle system 20 helps to aspirate a biological sample into needle system 20. Distal opening 316 of body 302 of restrictor 300 has a diameter than is smaller than the diameter of first bore 58 of needle slider 32. The small size of distal opening 316 of body 302 of restrictor 300 compared to first bore 58 of needle slider 32 inhibits solid material, such as the biological sample that is aspirated into needle system 20, from entering restrictor 300. Thus, solid material, such as the biological sample that is aspirated into needle system 20, is inhibited from being drawn into syringe 80.

Ribs 330 are positioned on restrictor 300 to provide structural support to restrictor 300. Ribs 330 are flexible and can be flattened when stylet 38 is positioned in restrictor 300. Slits 332 extending through body 302 and into an interior of ribs 330 help ribs 330 and restrictor 300 flatten when stylet 38 is positioned in restrictor 300. Ribs 330 also help to prevent cylindrical portion 312 of body 302 from inverting when stylet 38 is removed from needle system 20 and restrictor 300.

Restrictor 400 (FIGS. 10A-10B)

FIG. 10A is a perspective view of restrictor 400. FIG. 10B is a cross-sectional view of restrictor 400. Restrictor 400 includes body 402, rim 404, opening 406, and groove 408. Body 402 includes frustoconical portion 410, cylindrical portion 412, proximal opening 414, and distal opening 416. Rim 404 includes annulus portion 420 and flange portion 422. Restrictor 400 further includes plate 440.

Restrictor 400 has proximal end 400P and distal end 400D. Restrictor 400 includes body 402 and rim 404. Body 402 extends from proximal end 400P to distal end 400D of restrictor 400. Body 402 has proximal end 402P and distal end 402D. Rim 404 extends radially outward from proximal end 402P of body 402. Rim 404 has proximal end 404P and distal end 404D. Body 402 and rim 404 are integrally formed in the embodiment shown in FIGS. 10A-10B. In an alternate embodiment, body 402 and rim 404 can be two pieces that are connected together. Body 402 is hollow and has interior 406 extending from proximal end 402P to distal end 402D of body 402. Groove 408 is defined between body 402 and rim 404. Groove 408 has proximal end 408P and distal end 408D.

Body 402 of restrictor 400 includes frustoconical portion 410 and cylindrical portion 412. Frustoconical portion 410 forms proximal end 402P of body 402 and cylindrical portion 412 forms distal end 402D of body 402. Frustoconical portion 410 has proximal end 410P and distal end 410D, and cylindrical portion 412 has proximal end 412P and distal end 412D. Proximal end 410P of frustoconical portion 410 is aligned with proximal end 400P of restrictor 400, and distal end 412D of cylindrical portion 412 is aligned with distal end 400D of restrictor 400. Distal end 410D of frustoconical portion 410 is connected to proximal end 412P of cylindrical portion 412. Frustoconical portion 410 has a greater diameter at proximal end 410P and tapers to a smaller diameter at distal end 410D. Cylindrical portion 412 has a constant diameter from proximal end 412P to distal end 412D. The diameter of distal end 410D of frustoconical portion 410 is the same as the diameter of cylindrical portion 412. Proximal opening 414 is formed at proximal end 402P of body 402, and distal opening 416 is formed at distal end 402D of body 402. Proximal opening 414 has a greater diameter than a diameter of distal opening 416.

Rim 404 includes flange portion 420 and lip portion 422. Flange portion 420 extends radially outward from proximal end 410P of frustoconical portion 410 of body 402. Flange portion 420 is shaped like a flat ring. Flange portion 420 includes proximal end 420P and distal end 420D. A radially inner surface of rim 404 is connected to a radially outer surface of frustoconical portion 410 of body 402. Proximal end 420P of flange portion 420 is aligned with proximal end 404P of rim 404 and proximal end 400P of restrictor 400. Lip portion 422 is circumferential and extends in an axial direction away from distal end 420D of flange portion 420. Lip portion 422 includes proximal end 422P and distal end 422D. Lip portion 422 is shaped like a cylinder. Proximal end 422P of lip portion 422 is connected to distal end 420D of flange portion 420. Distal end 422D of lip portion 422 is aligned with distal end 404D of rim 404.

Interior 406 extends through frustoconical portion 410 and cylindrical portion 412 of body 402. A radially inner surface of frustoconical portion 410 and cylindrical portion 412 of body 402 form interior 406. Groove 408 is formed between frustoconical portion 410 of body 402, flange portion 420 of rim 404, and lip portion 422 of rim 404. Groove 408 is shaped like a ring. A radially outer surface of frustoconical portion 410 of body 402 defines a radially inner surface of groove 408; distal end 420D of flange portion 420 of rim 404 defines proximal end 408P of groove 408; and a radially inner surface of lip portion 422 of rim 404 defines a radially outer surface of groove 408. Distal end 408D of groove 408 is open.

Restrictor 400 further includes plate 440. Plate 440 extends radially outward from the distal end of body 402 of restrictor 400. Plate 440 is positioned around a distal end of cylindrical portion 412 of body 402. A radially inner surface of plate 440 is positioned around a radially outer surface of cylindrical portion 412. Plate 440 is annular shaped. A face of the proximal end 440D of plate 440 is flat and a face of the distal end 440D of plate 440 is beveled from the radially inner edge to the radially outer edge of plate 440.

Restrictor 400 is made of a flexible material, so that it is capable of being deformed. Restrictor 400 is made of a polymer, such as silicon rubber, plasticized polyvinyl chloride (PVC), or urethane, in the embodiment shows, but can be any suitable material in alternate embodiments. Cylindrical portion 412 of body 402 and distal end 410D of frustoconical portion 410 of body 402 can have the same or a slightly larger diameter than wire 72 of stylet 38. When stylet 38 is disposed in needle system 20, wire 72 of stylet 38 will extend through cylindrical portion 412 of body 402 and distal end 410D of frustoconical portion 410 of body 402. This allows both stylet 38 and restrictor 400 to be disposed in needle system 20 at the same time. Further, when syringe 80 is attached to aspiration port 52 of needle slider 32, restrictor 400 is secured between and a seal is formed between aspiration port 52 of needle slider 32 and syringe 80.

Interior 406 of restrictor 400 is aligned with and coaxial with first bore 58 of needle slider 32. Fluid can flow through interior 406 of body 402 of restrictor 400 between syringe 80 and needle system 20. This allows a vacuum to be created in needle system 20 using syringe 80. The vacuum in needle system 20 helps to aspirate a biological sample into needle system 20. Distal opening 416 of body 402 of restrictor 400 has a diameter than is smaller than the diameter of first bore 58 of needle slider 32. The small size of distal opening 416 of body 402 of restrictor 400 compared to first bore 58 of needle slider 32 inhibits solid material, such as the biological sample that is aspirated into needle system 20, from entering restrictor 400. Thus, solid material, such as the biological sample that is aspirated into needle system 20, is inhibited from being drawn into syringe 80.

Plate 440 is positioned on restrictor 400 to provide structural support to restrictor 400. Plate 440 helps to prevent cylindrical portion 412 of body 402 from inverting when stylet 38 is removed from needle system 20 and restrictor 400.

Restrictor 500 (FIGS. 11A-11B)

FIG. 11A is a perspective view of a proximal end of restrictor 500. FIG. 11B is a perspective view of a distal of restrictor 500. Restrictor 500 includes body 502, rim 504, opening 506, and groove 508. Body 502 includes frustoconical portion 510, cylindrical portion 512, proximal opening 514, and distal opening 516. Rim 504 includes annulus portion 520 and flange portion 522. Restrictor 500 further includes ribs 530 and holes 550.

Restrictor 500 has proximal end 500P and distal end 500D. Restrictor 500 includes body 502 and rim 504. Body 502 extends from proximal end 500P to distal end 500D of restrictor 500. Body 502 has proximal end 502P and distal end 502D. Rim 504 extends radially outward from proximal end 502P of body 502. Rim 504 has proximal end 504P and distal end 504D. Body 502 and rim 504 are integrally formed in the embodiment shown in FIGS. 11A-11B. In an alternate embodiment, body 502 and rim 504 can be two pieces that are connected together. Body 502 is hollow and has interior 506 extending from proximal end 502P to distal end 502D of body 502. Groove 508 is defined between body 502 and rim 504. Groove 508 has proximal end 508P and distal end 508D.

Body 502 of restrictor 500 includes frustoconical portion 510 and cylindrical portion 512. Frustoconical portion 510 forms proximal end 502P of body 502 and cylindrical portion 512 forms distal end 502D of body 502. Frustoconical portion 510 has proximal end 510P and distal end 510D, and cylindrical portion 512 has proximal end 512P and distal end 512D. Proximal end 510P of frustoconical portion 510 is aligned with proximal end 500P of restrictor 500, and distal end 512D of cylindrical portion 512 is aligned with distal end 500D of restrictor 500. Distal end 510D of frustoconical portion 510 is connected to proximal end 512P of cylindrical portion 512. Frustoconical portion 510 has a greater diameter at proximal end 510P and tapers to a smaller diameter at distal end 510D. Cylindrical portion 512 has a constant diameter from proximal end 512P to distal end 512D. The diameter of distal end 510D of frustoconical portion 510 is the same as the diameter of cylindrical portion 512. Proximal opening 514 is formed at proximal end 502P of body 502, and distal opening 516 is formed at distal end 502D of body 502. Proximal opening 514 has a greater diameter than a diameter of distal opening 516.

Rim 504 includes flange portion 520 and lip portion 522. Flange portion 520 extends radially outward from proximal end 510P of frustoconical portion 510 of body 502. Flange portion 520 is shaped like a flat ring. Flange portion 520 includes proximal end 520P and distal end 520D. A radially inner surface of rim 504 is connected to a radially outer surface of frustoconical portion 510 of body 502. Proximal end 520P of flange portion 520 is aligned with proximal end 504P of rim 504 and proximal end 500P of restrictor 500. Lip portion 522 is circumferential and extends in an axial direction away from distal end 520D of flange portion 520. Lip portion 522 includes proximal end 522P and distal end 522D. Lip portion 522 is shaped like a cylinder. Proximal end 522P of lip portion 522 is connected to distal end 520D of flange portion 520. Distal end 522D of lip portion 522 is aligned with distal end 504D of rim 504.

Interior 506 extends through frustoconical portion 510 and cylindrical portion 512 of body 502. A radially inner surface of frustoconical portion 510 and cylindrical portion 512 of body 502 form interior 506. Groove 508 is formed between frustoconical portion 510 of body 502, flange portion 520 of rim 504, and lip portion 522 of rim 504. Groove 508 is shaped like a ring. A radially outer surface of frustoconical portion 510 of body 502 defines a radially inner surface of groove 508; distal end 520D of flange portion 520 of rim 504 defines proximal end 508P of groove 508; and a radially inner surface of lip portion 522 of rim 504 defines a radially outer surface of groove 508. Distal end 508D of groove 508 is open.

Ribs 530 are positioned on restrictor 500. Ribs 530 extend radially outward from body 502 of restrictor 500. There are three ribs 530 positioned on body 502 in the embodiment shown in FIGS. 11A-11B, but any number of ribs 530 can be used in alternate embodiments. Ribs 530 extend along a portion of frustoconical portion 510 of body 502 and along cylindrical portion 512 of body 502. Ribs 530 each have a radially inner edge and a radially outer edge. The radially inner edge has a first portion that is beveled and connected to frustoconical portion 510 of body 502 and a second portion that is straight and connected to cylindrical portion 512 of body 502. The radially outer edge has a first portion that is straight that extends from proximal end 502P of body 502 and a second portion that beveled extending from the first portion to distal end 502D of body 502.

Restrictor 500 further includes holes 550 extending through body 502 of restrictor 500. There are three holes 550 shown in FIGS. 11A-11B, but any number of holes can be used in alternate embodiments. Holes 550 extend through frustoconical portion 510 of body 502. Holes 550 each extend from proximal end 500P to distal end 500D of restrictor 500 along an axis that is parallel to the axis on which restrictor 500 extends.

Restrictor 500 is made of a flexible material, so that it is capable of being deformed. Restrictor 500 is made of a polymer, such as silicon rubber, plasticized polyvinyl chloride (PVC), or urethane, in the embodiment shows, but can be any suitable material in alternate embodiments. Cylindrical portion 512 of body 502 and distal end 510D of frustoconical portion 510 of body 502 can have a diameter that is smaller than a diameter of wire 72 of stylet 38. When stylet 38 is disposed in needle system 20, restrictor 500 is deformed as cylindrical portion 512 of body 502 and distal end 510D of frustoconical portion 510 of body 502 are pushed outwards. This allows both stylet 38 and restrictor 500 to be disposed in needle system 20 at the same time. When stylet 38 is removed, restrictor 500 will resume its natural state. In an alternate embodiment, cylindrical portion 512 of body 502 and distal end 510D of frustoconical portion 510 of body 502 can have the same or a slightly larger diameter than wire 72 of stylet 38. Further, when syringe 80 is attached to aspiration port 52 of needle slider 32, restrictor 500 is secured between and a seal is formed between aspiration port 52 of needle slider 32 and syringe 80.

Interior 506 of restrictor 500 is aligned with and coaxial with first bore 58 of needle slider 32. Fluid can flow through interior 506 of body 502 of restrictor 500 between syringe 80 and needle system 20. This allows a vacuum to be created in needle system 20 using syringe 80. The vacuum in needle system 20 helps to aspirate a biological sample into needle system 20. Distal opening 516 of body 502 of restrictor 500 has a diameter than is smaller than the diameter of first bore 58 of needle slider 32. The small size of distal opening 516 of body 502 of restrictor 500 compared to first bore 58 of needle slider 32 inhibits solid material, such as the biological sample that is aspirated into needle system 20, from entering restrictor 500. Thus, solid material, such as the biological sample that is aspirated into needle system 20, is inhibited from being drawn into syringe 80.

Ribs 530 are positioned on restrictor 500 to provide structural support to restrictor 500. Ribs 530 are flexible and can be flattened when stylet 38 is positioned in restrictor 500. Ribs 530 also help to prevent cylindrical portion 512 of body 502 from inverting when stylet 38 is removed from needle system 20 and restrictor 500.

Holes 550 are included in frustoconical portion 510 of body 502 to allow air to move between syringe 80 and needle system 20. In the event a biological sample is aspirated through needle system 20 and blocks distal opening 516 of body 502, holes 550 allow the vacuum in needle system 20 to be maintained. This allows needle system 20 to continue aspirating a biological sample into needle 34.

Figures 12A, 12B:
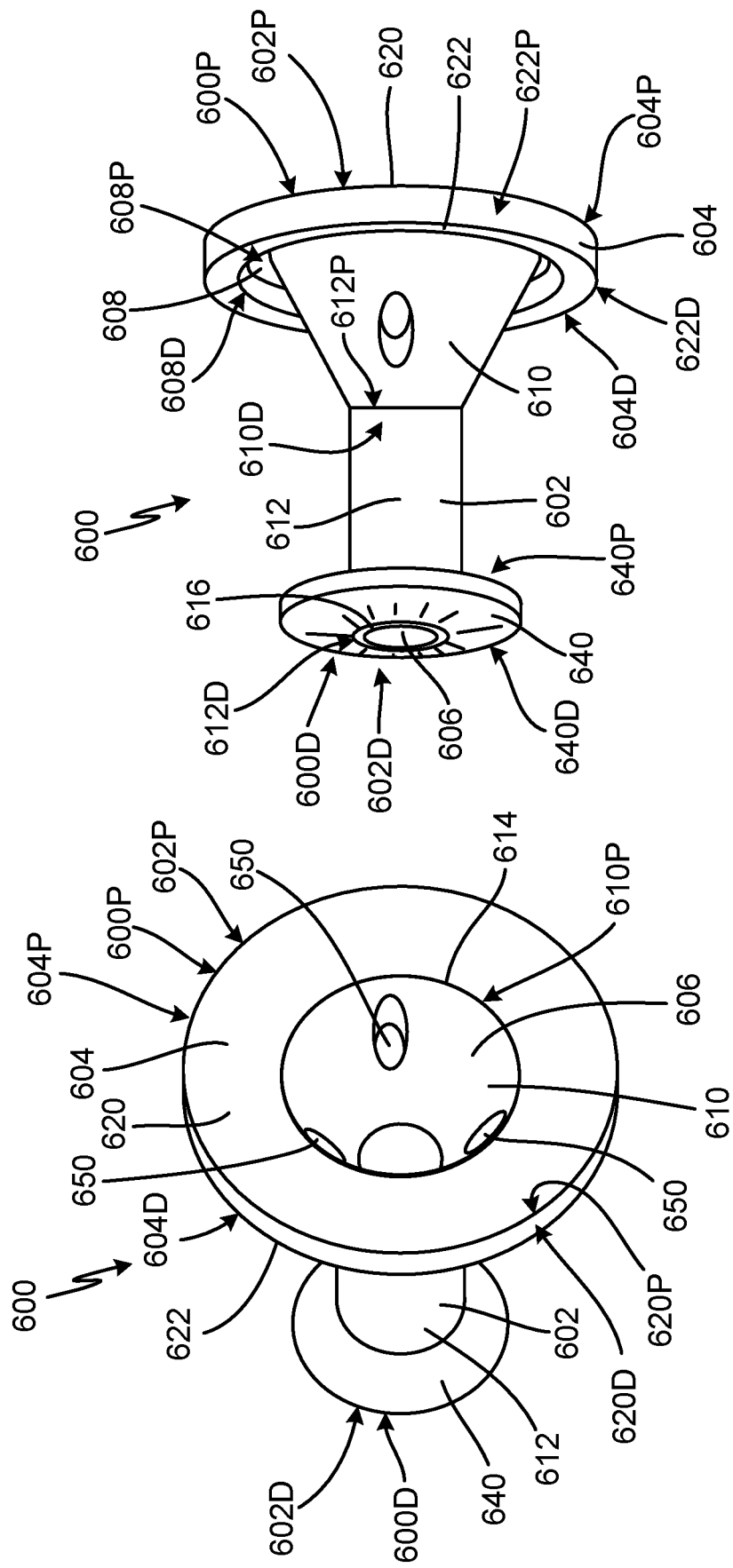
FIG. 12A is a perspective view of a proximal end of a sixth embodiment of the restrictor.
FIG. 12B is a perspective view of a distal end of the sixth embodiment of the restrictor.

Restrictor 600 (FIGS. 12A-12B)

FIG. 12A is a perspective view of a proximal end of a restrictor 600. FIG. 12B is a perspective view of a distal end of restrictor 600. Restrictor 600 includes body 602, rim 604, opening 606, and groove 608. Body 602 includes frustoconical portion 610, cylindrical portion 612, proximal opening 614, and distal opening 616. Rim 604 includes annulus portion 620 and flange portion 622. Restrictor 600 further includes plate 640 and holes 650.

Restrictor 600 has proximal end 600P and distal end 600D. Restrictor 600 includes body 602 and rim 604. Body 602 extends from proximal end 600P to distal end 600D of restrictor 600. Body 602 has proximal end 602P and distal end 602D. Rim 604 extends radially outward from proximal end 602P of body 602. Rim 604 has proximal end 604P and distal end 604D. Body 602 and rim 604 are integrally formed in the embodiment shown in FIGS. 12A-12B. In an alternate embodiment, body 602 and rim 604 can be two pieces that are connected together. Body 602 is hollow and has interior 606 extending from proximal end 602P to distal end 602D of body 602. Groove 608 is defined between body 602 and rim 604. Groove 608 has proximal end 608P and distal end 608D.

Body 602 of restrictor 600 includes frustoconical portion 610 and cylindrical portion 612. Frustoconical portion 610 forms proximal end 602P of body 602 and cylindrical portion 612 forms distal end 602D of body 602. Frustoconical portion 610 has proximal end 610P and distal end 610D, and cylindrical portion 612 has proximal end 612P and distal end 612D. Proximal end 610P of frustoconical portion 610 is aligned with proximal end 600P of restrictor 600, and distal end 612D of cylindrical portion 612 is aligned with distal end 600D of restrictor 600. Distal end 610D of frustoconical portion 610 is connected to proximal end 612P of cylindrical portion 612. Frustoconical portion 610 has a greater diameter at proximal end 610P and tapers to a smaller diameter at distal end 610D. Cylindrical portion 612 has a constant diameter from proximal end 612P to distal end 612D. The diameter of distal end 610D of frustoconical portion 610 is the same as the diameter of cylindrical portion 612. Proximal opening 614 is formed at proximal end 602P of body 602, and distal opening 616 is formed at distal end 602D of body 602. Proximal opening 614 has a greater diameter than a diameter of distal opening 616.

Rim 604 includes flange portion 620 and lip portion 622. Flange portion 620 extends radially outward from proximal end 610P of frustoconical portion 610 of body 602. Flange portion 620 is shaped like a flat ring. Flange portion 620 includes proximal end 620P and distal end 620D. A radially inner surface of rim 604 is connected to a radially outer surface of frustoconical portion 610 of body 602. Proximal end 620P of flange portion 620 is aligned with proximal end 604P of rim 604 and proximal end 600P of restrictor 600. Lip portion 622 is circumferential and extends in an axial direction away from distal end 620D of flange portion 620. Lip portion 622 includes proximal end 622P and distal end 622D. Lip portion 622 is shaped like a cylinder. Proximal end 622P of lip portion 622 is connected to distal end 620D of flange portion 620. Distal end 622D of lip portion 622 is aligned with distal end 604D of rim 604.

Interior 606 extends through frustoconical portion 610 and cylindrical portion 612 of body 602. A radially inner surface of frustoconical portion 610 and cylindrical portion 612 of body 602 form interior 606. Groove 608 is formed between frustoconical portion 610 of body 602, flange portion 620 of rim 604, and lip portion 622 of rim 604. Groove 608 is shaped like a ring. A radially outer surface of frustoconical portion 610 of body 602 defines a radially inner surface of groove 608; distal end 620D of flange portion 620 of rim 604 defines proximal end 608P of groove 608; and a radially inner surface of lip portion 622 of rim 604 defines a radially outer surface of groove 608. Distal end 608D of groove 608 is open.

Restrictor 600 further includes plate 640. Plate 640 extends radially outward from the distal end of body 602 of restrictor 600. Plate 640 is positioned around a distal end of cylindrical portion 612 of body 602. A radially inner surface of plate 640 is positioned around a radially outer surface of cylindrical portion 612. Plate 640 is annular shaped. A face of the proximal end 640D of plate 640 is flat and a face of the distal end 640D of plate 640 is beveled from the radially inner edge to the radially outer edge of plate 640.

Restrictor 600 further includes holes 650 extending through body 602 of restrictor 600. There are three holes 650 shown in FIGS. 12A-12B, but any number of holes can be used in alternate embodiments. Holes 650 extend through frustoconical portion 610 of body 602. Holes 650 each extend from proximal end 600P to distal end 600D of restrictor 600 along an axis that is parallel to the axis on which restrictor 600 extends.

Restrictor 600 is made of a flexible material, so that it is capable of being deformed. Restrictor 600 is made of a polymer, such as silicon rubber, plasticized polyvinyl chloride (PVC), or urethane, in the embodiment shows, but can be any suitable material in alternate embodiments. Cylindrical portion 612 of body 602 and distal end 610D of frustoconical portion 610 of body 602 can have the same or a slightly larger diameter than wire 72 of stylet 38. When stylet 38 is disposed in needle system 20, wire 72 of stylet 38 will extend through cylindrical portion 612 of body 602 and distal end 610D of frustoconical portion 610 of body 602. This allows both stylet 38 and restrictor 600 to be disposed in needle system 20 at the same time. Further, when syringe 80 is attached to aspiration port 52 of needle slider 32, restrictor 600 is secured between and a seal is formed between aspiration port 52 of needle slider 32 and syringe 80.

Interior 606 of restrictor 600 is aligned with and coaxial with first bore 58 of needle slider 32. Fluid can flow through interior 606 of body 602 of restrictor 600 between syringe 80 and needle system 20. This allows a vacuum to be created in needle system 20 using syringe 80. The vacuum in needle system 20 helps to aspirate a biological sample into needle system 20. Distal opening 616 of body 602 of restrictor 600 has a diameter than is smaller than the diameter of first bore 58 of needle slider 32. The small size of distal opening 616 of body 602 of restrictor 600 compared to first bore 58 of needle slider 32 inhibits solid material, such as the biological sample that is aspirated into needle system 20, from entering restrictor 600. Thus, solid material, such as the biological sample that is aspirated into needle system 20, is inhibited from being drawn into syringe 80.

Plate 640 is positioned on restrictor 600 to provide structural support to restrictor 600. Plate 640 helps to prevent cylindrical portion 612 of body 602 from inverting when stylet 38 is removed from needle system 20 and restrictor 600.

Holes 650 are included in frustoconical portion 610 of body 602 to allow air to move between syringe 80 and needle system 20. In the event a biological sample is aspirated through needle system 20 and blocks distal opening 616 of body 602, holes 650 allow the vacuum in needle system 20 to be maintained. This allows needle system 20 to continue aspirating a biological sample into needle 34.

Figures 13A, 13B:
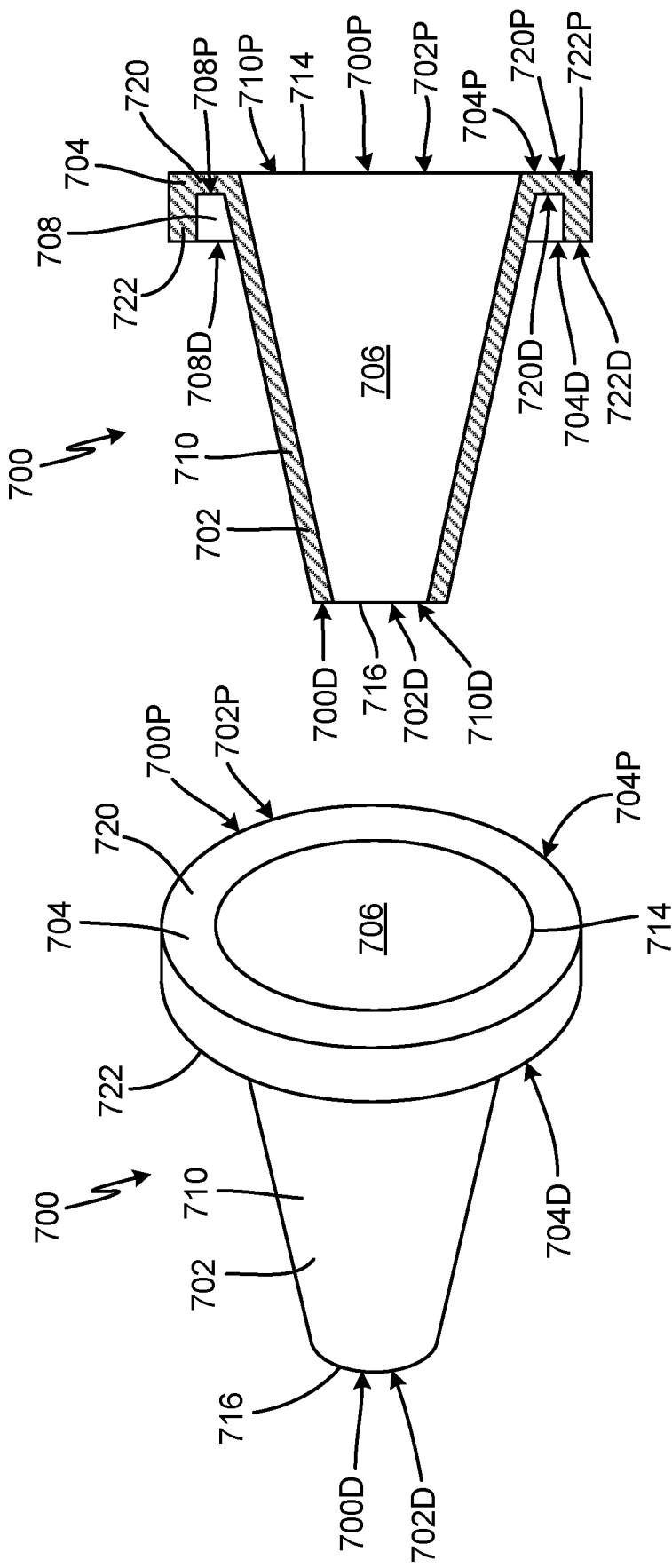
FIG. 13A is a perspective view of a seventh embodiment of the restrictor.
FIG. 13B is a cross-sectional view of the seventh embodiment of the restrictor.

Restrictor 700 (FIGS. 13A-13B)

FIG. 13A is a perspective view of restrictor 700. FIG. 13B is a cross-sectional view of restrictor 700. Restrictor 700 includes body 702, rim 704, opening 706, and groove 708. Body 702 includes frustoconical portion 710, proximal opening 714, and distal opening 716. Rim 704 includes flange portion 720 and lip portion 722.

Restrictor 700 has proximal end 700P and distal end 700D. Restrictor 700 includes body 702 and rim 704. Body 702 extends from proximal end 700P to distal end 700D of restrictor 700. Body 702 has proximal end 702P and distal end 702D. Rim 704 extends radially outward from proximal end 702P of body 702. Rim 704 has proximal end 704P and distal end 704D. Body 702 and rim 704 are integrally formed in the embodiment shown in FIGS. 13A-13B. In an alternate embodiment, body 702 and rim 704 can be two pieces that are connected together. Body 702 is hollow and has interior 706 extending from proximal end 702P to distal end 702D of body 702. Groove 708 is defined between body 702 and rim 704. Groove 708 has proximal end 708P and distal end 708D.

Body 702 of restrictor 700 includes frustoconical portion 710. Frustoconical portion 710 extends from proximal end 702P to distal end 702D of body 202. Frustoconical portion 710 has proximal end 710P and distal end 710D. Proximal end 710P of frustoconical portion 710 is aligned with proximal end 700P of restrictor 700, and distal end 710D of frustoconical portion 710 is aligned with distal end 700D of restrictor 700. Frustoconical portion 710 has a greater diameter at proximal end 710P and tapers to a smaller diameter at distal end 710D. Proximal opening 714 is formed at proximal end 702P of body 702, and distal opening 716 is formed at distal end 702D of body 702. Proximal opening 714 has a greater diameter than a diameter of distal opening 716.

Rim 704 includes flange portion 720 and lip portion 722. Flange portion 720 extends radially outward from proximal end 710P of frustoconical portion 710 of body 702. Flange portion 720 is shaped like a flat ring. Flange portion 720 includes proximal end 720P and distal end 720D. A radially inner surface of rim 704 is connected to a radially outer surface of frustoconical portion 710 of body 702. Proximal end 720P of flange portion 720 is aligned with proximal end 704P of rim 704 and proximal end 700P of restrictor 700. Lip portion 722 is circumferential and extends in an axial direction away from distal end 720D of flange portion 720. Lip portion 722 includes proximal end 722P and distal end 722D. Lip portion 722 is shaped like a cylinder. Proximal end 722P of lip portion 722 is connected to distal end 720D of flange portion 720. Distal end 722D of lip portion 722 is aligned with distal end 704D of rim 704.

Interior 706 extends through frustoconical portion 710 of body 202. A radially inner surface of frustoconical portion 710 of body 702 form interior 706. Groove 708 is formed between frustoconical portion 710 of body 702, flange portion 720 of rim 704, and lip portion 722 of rim 704. Groove 708 is shaped like a ring. A radially outer surface of frustoconical portion 710 of body 702 defines a radially inner surface of groove 708; distal end 720D of flange portion 720 of rim 704 defines proximal end 708P of groove 708; and a radially inner surface of lip portion 722 of rim 704 defines a radially outer surface of groove 708. Distal end 708D of groove 708 is open.

Restrictor 700 is made of a flexible material, so that it is capable of being deformed. Restrictor 700 is made of a polymer, such as silicon rubber, plasticized polyvinyl chloride (PVC), or urethane, in the embodiment shows, but can be any suitable material in alternate embodiments. Distal end 710D of frustoconical portion 710 of body 702 can have a diameter that is smaller than a diameter of wire 72 of stylet 38. When stylet 38 is disposed in needle system 20, restrictor 700 is deformed as distal end 710D of frustoconical portion 710 of body 702 is pushed outwards. This allows both stylet 38 and restrictor 700 to be disposed in needle system 20 at the same time. When stylet 38 is removed, restrictor 700 will resume its natural state. In an alternate embodiment, distal end 710D of frustoconical portion 710 of body 702 can have the same or a slightly larger diameter than wire 72 of stylet 38. Further, when syringe 80 is attached to aspiration port 52 of needle slider 32, restrictor 700 is secured between and a seal is formed between aspiration port 52 of needle slider 32 and syringe 80.

Interior 706 of restrictor 700 is aligned with and coaxial with first bore 78 of needle slider 32. Fluid can flow through interior 706 of body 702 of restrictor 700 between syringe 80 and needle system 20. This allows a vacuum to be created in needle system 20 using syringe 80. The vacuum in needle system 20 helps to aspirate a biological sample into needle system 20. Distal opening 716 of body 702 of restrictor 700 has a diameter than is smaller than the diameter of first bore 58 of needle slider 32. The small size of distal opening 716 of body 702 of restrictor 700 compared to first bore 58 of needle slider 32 inhibits solid material, such as the biological sample that is aspirated into needle system 20, from entering restrictor 700. Thus, solid material, such as the biological sample that is aspirated into needle system 20, is inhibited from being drawn into syringe 80.

Restrictor 800 (FIGS. 14A-14B)

FIG. 14A is a perspective view of restrictor 800. FIG. 14B is a cross-sectional view of restrictor 800. Restrictor 800 includes body 802, rim 804, opening 806, and groove 808. Body 802 includes cylindrical portion 812, proximal opening 814, and distal opening 816. Rim 804 includes flange portion 820 and lip portion 822.

Restrictor 800 has proximal end 800P and distal end 800D. Restrictor 800 includes body 802 and rim 804. Body 802 extends from proximal end 800P to distal end 800D of restrictor 800. Body 802 has proximal end 802P and distal end 802D. Rim 804 extends radially outward from proximal end 802P of body 802. Rim 804 has proximal end 804P and distal end 804D. Body 802 and rim 804 are integrally formed in the embodiment shown in FIGS. 14A-14B. In an alternate embodiment, body 802 and rim 804 can be two pieces that are connected together. Body 802 is hollow and has interior 806 extending from proximal end 802P to distal end 802D of body 802. Groove 808 is defined between body 802 and rim 804. Groove 808 has proximal end 808P and distal end 808D.

Body 802 of restrictor 800 includes cylindrical portion 812. Cylindrical portion 812 extends from proximal end 802P to distal end 802D of body 802. Cylindrical portion 812 has proximal end 812P and distal end 812D. Proximal end 812P of cylindrical portion 812 is aligned with proximal end 800P of restrictor 800, and distal end 812D of cylindrical portion 812 is aligned with distal end 800D of restrictor 800. Cylindrical portion 812 has a constant diameter from proximal end 812P to distal end 812D. Proximal opening 814 is formed at proximal end 802P of body 802, and distal opening 816 is formed at distal end 802D of body 802. Proximal opening 814 has a greater diameter than a diameter of distal opening 816.

Rim 804 includes flange portion 820 and lip portion 822. Flange portion 820 extends radially outward from proximal end 810P of frustoconical portion 810 of body 802. Flange portion 820 is shaped like a flat ring. Flange portion 820 includes proximal end 820P and distal end 820D. A radially inner surface of rim 804 is connected to a radially outer surface of frustoconical portion 810 of body 802. Proximal end 820P of flange portion 820 is aligned with proximal end 804P of rim 804 and proximal end 800P of restrictor 800. Lip portion 822 is circumferential and extends in an axial direction away from distal end 820D of flange portion 820. Lip portion 822 includes proximal end 822P and distal end 822D. Lip portion 822 is shaped like a cylinder. Proximal end 822P of lip portion 822 is connected to distal end 820D of flange portion 820. Distal end 822D of lip portion 822 is aligned with distal end 804D of rim 204.

Interior 806 extends through cylindrical portion 812 of body 802. A radially inner surface of cylindrical portion 812 of body 802 forms interior 806. Groove 808 is formed between cylindrical portion 812 of body 802, flange portion 820 of rim 804, and lip portion 822 of rim 804. Groove 808 is shaped like a ring. A radially outer surface of cylindrical portion 812 of body 802 defines a radially inner surface of groove 808; distal end 820D of flange portion 820 of rim 804 defines proximal end 808P of groove 808; and a radially inner surface of lip portion 822 of rim 804 defines a radially outer surface of groove 808. Distal end 808D of groove 808 is open.

Restrictor 800 is made of a flexible material, so that it is capable of being deformed. Restrictor 800 is made of a polymer, such as silicon rubber, plasticized polyvinyl chloride (PVC), or urethane, in the embodiment shows, but can be any suitable material in alternate embodiments. Cylindrical portion 812 of body 802 can have a diameter that is smaller than a diameter of wire 72 of stylet 38. When stylet 38 is disposed in needle system 20, restrictor 800 is deformed as cylindrical portion 812 of body 802 is pushed outwards. This allows both stylet 38 and restrictor 800 to be disposed in needle system 20 at the same time. When stylet 38 is removed, restrictor 800 will resume its natural state. In an alternate embodiment, cylindrical portion 812 of body 802 can have the same or a slightly larger diameter than wire 72 of stylet 38. Further, when syringe 80 is attached to aspiration port 52 of needle slider 32, restrictor 800 is secured between and a seal is formed between aspiration port 52 of needle slider 32 and syringe 80.

Interior 806 of restrictor 800 is aligned with and coaxial with first bore 58 of needle slider 32. Fluid can flow through interior 806 of body 802 of restrictor 800 between syringe 80 and needle system 20. This allows a vacuum to be created in needle system 20 using syringe 80. The vacuum in needle system 20 helps to aspirate a biological sample into needle system 20. Distal opening 816 of body 802 of restrictor 800 has a diameter than is smaller than the diameter of first bore 58 of needle slider 32. The small size of distal opening 816 of body 802 of restrictor 800 compared to first bore 58 of needle slider 32 inhibits solid material, such as the biological sample that is aspirated into needle system 20, from entering restrictor 800. Thus, solid material, such as the biological sample that is aspirated into needle system 20, is inhibited from being drawn into syringe 80.

Figure 15:
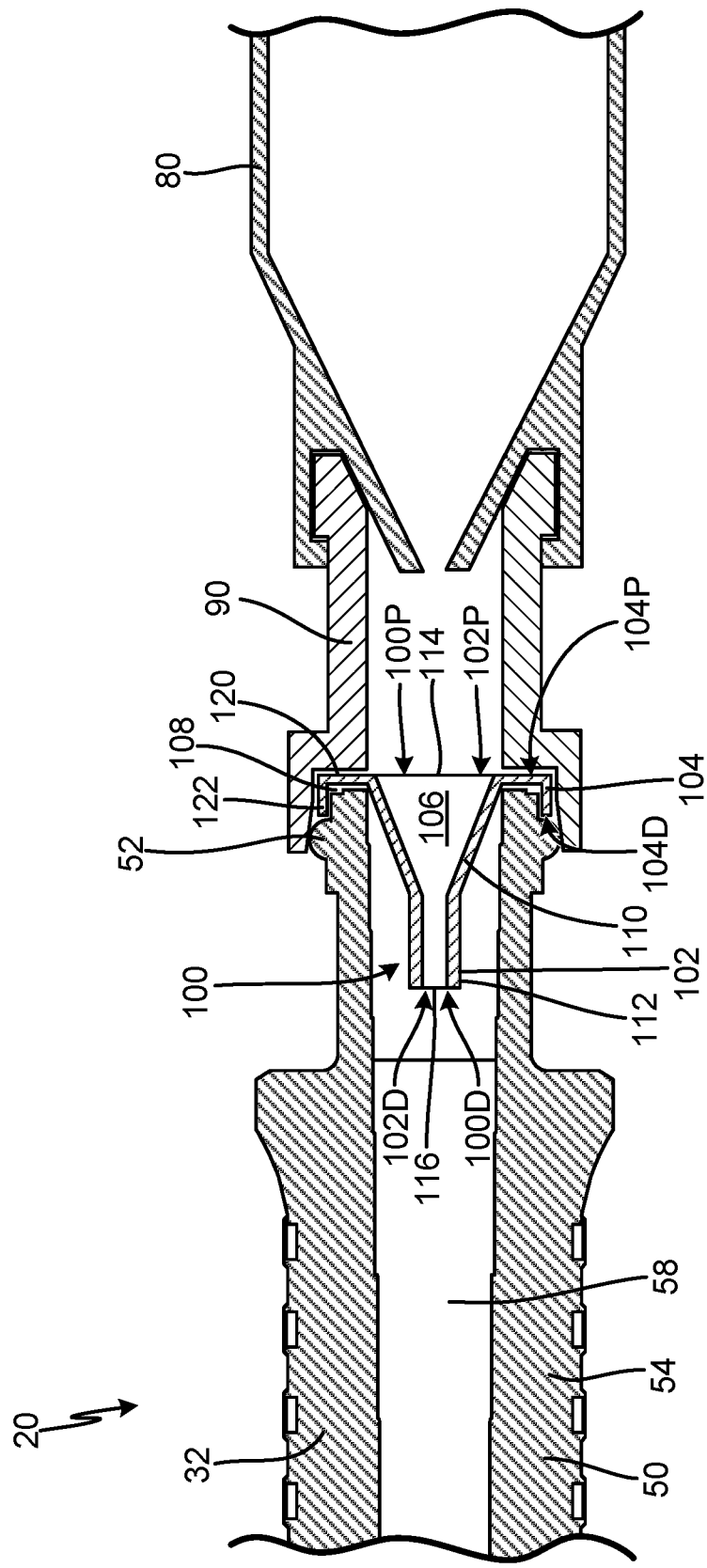
FIG. 15 is a cross-sectional view of the restrictor in the needle slider with a cap piece and a syringe attached.

FIG. 15 is a cross-sectional view of restrictor 100 in needle slider 32 with cap piece 90 and syringe 80 attached. FIG. 15 shows needle slider 32, housing 50, aspiration port 52, grip 54, and first bore 58 of needle system 20. FIG. 15 also shows syringe 80, cap piece 90, and restrictor 100. Restrictor 100 includes body 102, rim 104, interior 106, and groove 108. Body 102 includes frustoconical portion 110, cylindrical portion 112, proximal opening 114, and distal opening 116. Rim 104 includes flange portion 120 and lip portion 122.

Needle slider 32 has the structure as described in reference to FIGS. 1A-5 above. Syringe 80 is connected to cap piece 90 with luer fittings. Cap piece 90 is fit around aspiration port 52 of needle slider 32 and affixed to aspiration port 52 of needle slider 32. For example, cap piece 90 can be affixed to aspiration port 52 of needle slider 32 with an adhesive or by ultrasonic welding. Restrictor 100 is disposed in aspiration port 52 of needle slider 32 of needle system 20. Restrictor 100 has the structure as describe in reference to FIGS. 6A-7B above. Restrictor 100 is described for use with needle system 20 shown in FIGS. 1A-6C, but restrictor 100 can be used with any needle system in alternate embodiments.

Restrictor 100 is disposed in needle system 20 so that body 102 of restrictor 100 is disposed in first bore 58 of needle slider 32 and rim 104 of restrictor 100 sits around proximal end 132P of aspiration port 132. Proximal end 132P of aspiration port 132 thus sits in groove 108 of restrictor 100. Cap piece 90 is positioned around and affixed to aspiration port 52 of needle slider 32 to secure restrictor 100 in aspiration port 52 of needle slider 82 and form a seal between aspiration port 52 and cap piece 90. Cap piece 90 allows any form of syringe 80 to be used with needle system 20 when needle system 20 includes restrictor 100.

Interior 106 of restrictor 100 is aligned with and coaxial with first bore 58 of needle slider 32. Fluid can flow through interior 106 of body 102 of restrictor 100 between syringe 80 and needle system 20 through cap piece 90. This allows a vacuum to be created in needle system 20 using syringe 80. The vacuum in needle system 20 helps to aspirate a biological sample into needle system 20. Distal opening 116 of body 102 of restrictor 100 has a diameter than is smaller than the diameter of first bore 58 of needle slider 32. The small size of distal opening 116 of body 102 of restrictor 100 compared to first bore 58 of needle slider 32 inhibits solid material, such as the biological sample that is aspirated into needle system 20, from entering restrictor 100. Thus, solid material, such as the biological sample that is aspirated into needle system 20, is inhibited from being drawn into cap piece 90 and syringe 80.

Discussion of Possible Embodiments

The following are non-exclusive descriptions of possible embodiments of the present invention.

A needle system a handle and a needle slider partially positioned in the handle. The needle slider has an aspiration port at a proximal end of the needle slider. A needle connected to and extending away from the needle slider. A restrictor is disposed in the aspiration port of the needle slider. The restrictor is configured to inhibit passage of a sample through the aspiration port.

The needle system of the preceding paragraph can optionally include, additionally and/or alternatively, any one or more of the following features, configurations and/or additional components:

The restrictor is made of a flexible material.

The restrictor permits fluid flow through the restrictor, and inhibits solid material from moving into the restrictor.

The restrictor includes a hollow body with a proximal end having a proximal opening and a distal end having a distal opening, and a rim extending from the proximal end of the body having a radial flange portion and a circumferential lip portion.

The rim of the restrictor is positioned around an outer diameter of the aspiration port of the needle slider.

The needle system further comprises a syringe connected to the aspiration port of the needle slider.

The restrictor forms a seal between the needle system and the syringe.

A diameter of the proximal opening of the hollow body is larger than a diameter of the distal opening of the hollow body.

The hollow body includes a frustoconical portion with a proximal end aligned with the proximal end of the hollow body and a distal end, and a cylindrical portion with a proximal end extending from the distal end of the frustoconical portion and a distal end aligned with the distal end of the hollow body.

The radial flange portion of the rim has a proximal end aligned with a proximal end of the rim and a distal end, and the circumferential lip portion of the rim has a proximal end extending from the distal end of the radial flange portion and a distal end aligned with a distal end of the rim.

The needle system further includes one or more ribs extending from the hollow body.

There is a slit cut through the hollow body and into an interior of one of the ribs.

The needle system further includes a plate extending around the distal end of the hollow body.

The needle system further includes a hole extending through the hollow body.

The needle system further includes a sheath connected to and extending away from the handle, and a stylet extending through the needle. The needle is positioned in and movable in the sheath. The stylet is positioned in an interior of the hollow body of the restrictor and deforms the restrictor.

The needle slider is movable in the handle and further includes a grip, and a shaft that is movable in the handle.

The syringe is positioned around the rim of the restrictor.

The rim is configured to secure the restrictor between the syringe and the needle system.

A groove is defined by the hollow body, the radial flange portion of the rim, and the circumferential lip portion of the rim.

The groove is positioned around the proximal end of the needle slider.

An outer diameter of the groove is larger than an outer diameter of the proximal opening of the hollow body.

A diameter of the proximal end of the frustoconical portion is greater than a diameter of the distal end of the frustoconical portion and the frustoconical portion tapers from the proximal end to the distal end.

The proximal end of the frustoconical portion of the hollow body is aligned with the proximal end of the needle slider.

An inner diameter of the radial flange portion of the rim extends from an outer diameter of the frustoconical portion of the hollow body.

The groove is annular shaped.

An outer diameter of the groove is defined by an inner diameter of the circumferential lip portion of the rim, wherein an inner diameter of the groove is defined by the outer diameter of the frustoconical portion of the hollow body, and wherein a proximal end of the groove is defined by the distal end of the radial flange portion of the rim.

The rib extends along the frustoconical portion and the cylindrical portion of the hollow body.

A radially outer edge of the rib has a straight portion extending from the proximal end of the hollow body.

The radially outer edge of a rib has a beveled portion extending from the straight portion of the radially outer edge of the rib to the distal end of the hollow body.

A radially inner edge of the rib has a beveled portion extending along the frustoconical portion of the body and a straight portion extending along the cylindrical portion of the body.

The plate is annular shaped with a beveled face on a distal end of the plate.

The hole extends through the frustoconical portion of the hollow body.

A restrictor includes a hollow body with a proximal end having a proximal opening and a distal end having a distal opening. The hollow body is configured to fit into an aspiration port of a needle slider. A rim extends from the proximal end of the body. The rim is configured to form a seal between a syringe and the needle slider at the aspiration port.

The restrictor of the preceding paragraph can optionally include, additionally and/or alternatively, any one or more of the following features, configurations and/or additional components:

The restrictor is made out of a flexible material.

The diameter of the proximal opening of the hollow body is larger than a diameter of the distal opening of the hollow body.

The hollow body includes a frustoconical portion with a proximal end aligned with the proximal end of the hollow body and a distal end, and a cylindrical portion with a proximal end extending from the distal end of the frustoconical portion and a distal end aligned with the distal end of the hollow body.

The rim includes a radial flange portion with a proximal end aligned with a proximal end of the rim and a distal end, and a circumferential lip portion with a proximal end extending from the distal end of the radial flange portion and a distal end aligned with a distal end of the rim.

An inner diameter of the radial flange portion of the rim extends from an outer diameter of the frustoconical portion of the hollow body.

A groove is defined by the hollow body, the radial flange portion of the rim, and the circumferential lip portion of the rim.

The restrictor further includes one or more ribs extending from the hollow body.

There is a slit cut through the hollow body and into an interior of the rib.

The restrictor further includes a plate extending around the distal end of the hollow body.

The restrictor further includes a hole extending through the hollow body.

A diameter of the groove is larger than a diameter of the proximal opening of the hollow body.

A diameter of the proximal end of the frustoconical portion is greater than a diameter of the distal end of the frustoconical portion and the frustoconical portion tapers from the proximal end to the distal end.

The groove is annular shaped.

An outer diameter of the groove is defined by an inner diameter of the circumferential lip portion of the rim, wherein an inner diameter of the groove is defined by the outer diameter of the frustoconical portion of the hollow body, and wherein a proximal end of the groove is defined by the distal end of the radial flange portion of the rim.

The rib extends along the frustoconical portion and the cylindrical portion of the hollow body.

A radially outer edge of the rib has a straight portion extending from the proximal end of the hollow body.

The radially outer edge of a rib has a beveled portion extending from the straight portion of the radially outer edge of the rib to the distal end of the hollow body.

A radially inner edge of the rib has a beveled portion extending along the frustoconical portion of the body and a straight portion extending along the cylindrical portion of the body.

The plate is annular shaped with a beveled face on a distal end of the plate.

The hole extends through the frustoconical portion of the hollow body.

A method includes positioning a restrictor in a needle system. The needle system has a handle, a needle slider partially positioned in the handle, a sheath secured in the handle, and a needle secured in the needle slider and extending through the sheath. The needle of the needle slider is advanced out of the sheath and into a sample. A syringe is connected to an aspiration port of the needle slider of the needle system. The sample is aspirated into the needle of the needle system. The sample is inhibited, with the restrictor, from moving into the syringe.

The method of the preceding paragraph can optionally include, additionally and/or alternatively, any one or more of the following features, configurations and/or additional components:

Positioning the restrictor in the needle system includes positioning the restrictor in the aspiration port of the needle slider of the needle system.

The method further includes applying suction to the syringe, and creating a vacuum in the needle system.

Inhibiting the sample from moving into the syringe includes restricting the diameter of a flow path in the needle system with the restrictor.

The method further includes removing a stylet from the needle system.

Aspirating the sample into the needle includes moving the needle slider of the needle system to move the needle in the sample.

A restrictor includes a hollow body with a proximal end having a proximal opening and a distal end having a distal opening, and a rim extending from the proximal end of the body. The hollow body is configured to fit into a lumen. The rim is configured to form a proximal seal on a proximal face of the rim and a distal seal on a distal face of the rim.

The restrictor of the preceding paragraph can optionally include, additionally and/or alternatively, any one or more of the following features, configurations and/or additional components:

The hollow body is configured to fit into an aspiration port of a needle slider, and the rim is configured to form a seal between a syringe and the needle slider at the aspiration port.

The restrictor is made out of a flexible material.

The rim has a radial flange portion and a circumferential lip portion, a groove being defined by the hollow body, the radial flange portion of the rim, and the circumferential lip portion of the rim.

A diameter of the groove is larger than a diameter of the proximal opening of the hollow body.

The diameter of the proximal opening of the hollow body is larger than a diameter of the distal opening of the hollow body.

The radial flange portion of the rim has a proximal end aligned with a proximal end of the rim and a distal end, and the circumferential lip portion of the rim has a proximal end extending from the distal end of the radial flange portion and a distal end aligned with a distal end of the rim.

An inner diameter of the radial flange portion of the rim extends from an outer diameter of the hollow body.

The groove is annular shaped.

An outer diameter of the groove is defined by an inner diameter of the circumferential lip portion of the rim, wherein an inner diameter of the groove is defined by the outer diameter of the hollow body, and wherein a proximal end of the groove is defined by the distal end of the radial flange portion of the rim.

The restrictor further includes one or more ribs extending from the hollow body.

A radially outer edge of the rib has a straight portion extending from the proximal end of the hollow body.

The restrictor further includes a plate extending around the distal end of the hollow body.

The plate is annular shaped with a beveled face on a distal end of the plate.

The restrictor further includes one or more holes extending through the hollow body.

A restrictor includes a hollow body with a proximal end having a proximal opening and a distal end having a distal opening. The diameter of the proximal opening of the hollow body is larger than a diameter of the distal opening of the hollow body. The hollow body is configured to fit into a lumen. The restrictor is secured to the lumen at the proximal end. The diameter of the proximal opening of the hollow body is larger than a diameter of the distal opening of the hollow body.

The restrictor of the preceding paragraph can optionally include, additionally and/or alternatively, any one or more of the following features, configurations and/or additional components:

The restrictor is made out of a flexible material.

The hollow body includes a frustoconical portion with a proximal end aligned with the proximal end of the hollow body and a distal end, and a cylindrical portion with a proximal end extending from the distal end of the frustoconical portion and a distal end aligned with the distal end of the hollow body.

A diameter of the proximal end of the frustoconical portion is greater than a diameter of the distal end of the frustoconical portion and the frustoconical portion tapers from the proximal end to the distal end.

The radial flange portion of the rim has a proximal end aligned with a proximal end of the rim and a distal end, and the circumferential lip portion of the rim has a proximal end extending from the distal end of the radial flange portion and a distal end aligned with a distal end of the rim.

The restrictor further includes a rib extending from the hollow body.

The rib extends along the frustoconical portion and the cylindrical portion of the hollow body.

A radially outer edge of the rib has a straight portion extending from the proximal end of the hollow body.

The radially outer edge of the rib has a chamfered portion extending from the straight portion of the radially outer edge of the rib to the distal end of the hollow body.

A radially inner edge of the rib has a beveled portion extending along the frustoconical portion of the body and a straight portion extending along the cylindrical portion of the hollow body.

The restrictor is made out of a flexible material and wherein there is a slit cut through the hollow body and into an interior of the rib.

The restrictor further includes a plate extending around the distal end of the hollow body.

The plate is annular shaped with a beveled face on a distal end of the plate.

A plurality of ribs extend from the hollow body.

The restrictor further includes a hole extending through the hollow body.

The hole extends through the frustoconical portion of the hollow body.

A restrictor includes a hollow body with a proximal end having a proximal opening and a distal end having a distal opening. The hollow body is configured to fit into a lumen. A rib extending from the hollow body. The restrictor is secured to the lumen at the proximal end.

The restrictor of the preceding paragraph can optionally include, additionally and/or alternatively, any one or more of the following features, configurations and/or additional components:

The restrictor is made out of a flexible material

The hollow body includes a frustoconical portion with a proximal end aligned with the proximal end of the hollow body and a distal end, and a cylindrical portion with a proximal end extending from the distal end of the frustoconical portion and a distal end aligned with the distal end of the hollow body.

The rib extends along the frustoconical portion and the cylindrical portion of the hollow body.

A radially outer edge of the rib has a straight portion extending from the proximal end of the hollow body.

The radially outer edge of the rib has a beveled portion extending from the straight portion of the radially outer edge of the rib to the distal end of the hollow body.

A radially inner edge of the rib has a beveled portion extending along the frustoconical portion of the body and a straight portion extending along the cylindrical portion of the hollow body.

There is a slit cut through the hollow body and into an interior of the rib.

A plurality of ribs extend from the hollow body.

The restrictor further includes a hole extending through the hollow body.

The hole extends through the frustoconical portion of the hollow body.

A restrictor includes a hollow body with a proximal end having a proximal opening and a distal end having a distal opening. The hollow body is configured to fit into a lumen. A plate extending around the distal end of the hollow body. The restrictor is secured to the lumen at the proximal end.

The restrictor of the preceding paragraph can optionally include, additionally and/or alternatively, any one or more of the following features, configurations and/or additional components:

The restrictor is made out of a flexible material.

The restrictor further includes a rim extending from the proximal end of the body, wherein the rim is configured to form a proximal seal on a proximal face of the rime and a distal seal on a distal face of the rim.

The diameter of the proximal opening of the hollow body is larger than a diameter of the distal opening of the hollow body.

The hollow body includes a frustoconical portion with a proximal end aligned with the proximal end of the hollow body and a distal end, and a cylindrical portion with a proximal end extending from the distal end of the frustoconical portion and a distal end aligned with the distal end of the hollow body.

The plate is annular shaped with a beveled face on a distal end of the plate.

The restrictor further includes a hole extending through the hollow body.

The hole extends through the frustoconical portion of the hollow body.

While the invention has been described with reference to an exemplary embodiment(s), it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment(s) disclosed, but that the invention will include all embodiments falling within the scope of the appended claims.

The invention claimed is:

1. A needle system comprising:
   a handle;
   a needle slider partially positioned in the handle, the needle slider having an aspiration port at a proximal end of the needle slider and an internal lumen extending therethrough;
   a needle connected to and extending away from the needle slider; and
   a restrictor disposed in the aspiration port of the needle slider and extending distally into the internal lumen of the needle slider, the restrictor being configured to inhibit passage of a sample through the aspiration port, wherein the restrictor comprises:
      a hollow body with a proximal end having a proximal opening and a distal end having a distal opening; and
      a rim extending from the proximal end of the body having a radial flange portion and a circumferential lip portion, wherein the rim of the restrictor is positioned around an outer diameter of the aspiration port of the needle slider.

2. The needle system of claim 1, wherein the restrictor is made of a flexible material.

3. The needle system of claim 1, wherein the restrictor permits fluid flow through the restrictor, and inhibits solid material from moving into the restrictor.

4. The needle system of claim 1, and further comprising:
   a syringe connected to the aspiration port of the needle slider, wherein the restrictor forms a seal between the needle system and the syringe.

5. The needle system of claim 1, wherein a diameter of the proximal opening of the hollow body is larger than a diameter of the distal opening of the hollow body.

6. The needle system of claim 1, wherein the hollow body comprises:
   a frustoconical portion with a proximal end aligned with the proximal end of the hollow body and a distal end; and
   a cylindrical portion with a proximal end extending from the distal end of the frustoconical portion and a distal end aligned with the distal end of the hollow body.

7. The needle system of claim 1, and further comprising: one or more ribs extending from the hollow body.

8. The needle system of claim 7, wherein there is a slit cut through the hollow body and into an interior of one of the ribs.

9. The needle system of claim 1, and further comprising: a plate extending around the distal end of the hollow body.

10. The needle system of claim 1, and further comprising: a hole extending through the hollow body.

11. The needle system of claim 1, and further comprising:
    a sheath connected to and extending away from the handle, wherein the needle is positioned in and movable in the sheath; and
    a stylet extending through the needle, wherein the stylet is positioned in an interior of the hollow body of the restrictor and deforms the restrictor.

12. The needle system of claim 1, wherein the needle slider is movable in the handle and further comprises:
    a grip; and
    a shaft that is movable in the handle.

13. A restrictor comprising:
    a hollow body with a proximal end having a proximal opening and a distal end having a distal opening, wherein the hollow body is configured to fit into an aspiration port of a needle slider and comprises:
       a frustoconical portion with a proximal end aligned with the proximal end of the hollow body and a distal end; and
       cylindrical portion with a proximal end extending from the distal end of the frustoconical portion and a distal end aligned with the distal end of the hollow body; and
    a rim extending from the proximal end of the body, wherein the rim is configured to form a seal between a syringe and the needle slider at the aspiration port and comprises:
       a radial flange portion with a proximal end aligned with a proximal end of the rim and a distal end; and
       a circumferential lip portion with a proximal end extending from the distal end of the radial flange portion and a distal end aligned with a distal end of the rim.

14. The restrictor of claim 13, wherein an inner diameter of the radial flange portion of the rim extends from an outer diameter of the frustoconical portion of the hollow body, and wherein a groove is defined by the hollow body, the radial flange portion of the rim, and the circumferential lip portion of the rim.

15. A needle system comprising:
    a handle;
    a needle slider partially positioned in the handle, the needle slider having an aspiration port at a proximal end of the needle slider and an internal lumen extending therethrough;
    a needle connected to and extending away from the needle slider; and
    a restrictor disposed in the aspiration port of the needle slider and extending distally into the internal lumen of the needle slider, the restrictor being configured to inhibit passage of a sample through the aspiration port, wherein the restrictor comprises:
       a hollow body with a proximal end having a proximal opening and a distal end having a distal opening, wherein the hollow body comprises:
          a frustoconical portion with a proximal end aligned with the proximal end of the hollow body and a distal end; and
          a cylindrical portion with a proximal end extending from the distal end of the frustoconical portion and a distal end aligned with the distal end of the hollow body; and a rim extending from the proximal end of the body having a radial flange portion and a circumferential lip portion.

\* \* \* \* \*